US011039962B2

(12) United States Patent
Squitieri

(10) Patent No.: US 11,039,962 B2
(45) Date of Patent: *Jun. 22, 2021

(54) NON-INVASIVE PRESSURE-MITIGATION APPARATUSES FOR IMPROVING BLOOD FLOW AND ASSOCIATED SYSTEMS AND METHODS

(71) Applicant: TurnCare, Inc., Palo Alto, CA (US)

(72) Inventor: Rafael Paolo Squitieri, Wilton, CT (US)

(73) Assignee: TURNCARE, INC., Palo Alto, CA (US)

(*) Notice: Subject to any disclaimer, the term of this patent is extended or adjusted under 35 U.S.C. 154(b) by 447 days.

This patent is subject to a terminal disclaimer.

(21) Appl. No.: 16/142,625

(22) Filed: Sep. 26, 2018

(65) Prior Publication Data

US 2019/0021918 A1 Jan. 24, 2019

Related U.S. Application Data

(63) Continuation-in-part of application No. 15/905,649, filed on Feb. 26, 2018, now Pat. No. 10,751,229,
(Continued)

(51) Int. Cl.
*A61F 13/06* (2006.01)
*A47C 27/08* (2006.01)
(Continued)

(52) U.S. Cl.
CPC .......... *A61F 13/51474* (2013.01); *A61F 5/32* (2013.01); *A61F 5/34* (2013.01);
(Continued)

(58) Field of Classification Search
CPC ...... A61G 7/05; A61G 7/001; A61G 7/05776; A61G 7/1021; A61M 25/02
(Continued)

(56) References Cited

U.S. PATENT DOCUMENTS 4,536,893 A    8/1985   Parravicini et al.
4,567,887 A    2/1986   Couch, Jr.
(Continued)

FOREIGN PATENT DOCUMENTS

EP    2000057 A1    12/2008
WO   9808473 A1     3/1998
(Continued)

OTHER PUBLICATIONS

Canadian Office Action dated Nov. 17, 2020 for Canadian Application No. 2,865,843, 5 pages.

*Primary Examiner* — Tarla R Patel
(74) *Attorney, Agent, or Firm* — Perkins Coie LLP

(57) ABSTRACT

Introduced here are apparatuses and systems for mitigating contact pressures applied to a human body by the surface of an object, such as a chair, bed, or table. A pressure-mitigation apparatus can include a series of chambers whose pressure can be individually varied. When placed between a patient and a contact surface, the pressure-mitigation apparatus can vary the contact pressure on a specific anatomical region of the patient by controllably inflating and/or deflating one or more cell. Moreover, a pressure-mitigation system can be readily integrated into a conventional treatment regimen for a variety of different conditions.

20 Claims, 12 Drawing Sheets

Related U.S. Application Data which is a continuation of application No. 14/313,570, filed on Jun. 24, 2014, now Pat. No. 9,901,491, which is a continuation of application No. 14/063,861, filed on Oct. 25, 2013, now Pat. No. 8,757,165, which is a continuation-in-part of application No. 13/660,429, filed on Oct. 25, 2012, now abandoned.

(60) Provisional application No. 61/618,936, filed on Apr. 2, 2012, provisional application No. 62/647,551, filed on Mar. 23, 2018.

(51) Int. Cl.

| | | |
|---|---|---|
| *A61F 13/514* | (2006.01) | |
| *A61F 5/32* | (2006.01) | |
| *A61F 5/34* | (2006.01) | |
| *A61G 7/057* | (2006.01) | |
| *A61G 7/07* | (2006.01) | |
| *A61F 13/15* | (2006.01) | |
| *A61F 13/505* | (2006.01) | |
| *A61F 13/512* | (2006.01) | |
| *A61F 13/513* | (2006.01) | |
| *A61F 13/515* | (2006.01) | |
| *A61F 13/64* | (2006.01) | |
| *A61F 13/84* | (2006.01) | |
| *A61G 7/05* | (2006.01) | |

(52) U.S. Cl.
CPC ...... *A61F 13/15203* (2013.01); *A61F 13/505* (2013.01); *A61F 13/512* (2013.01); *A61F 13/513* (2013.01); *A61F 13/515* (2013.01); *A61F 13/51456* (2013.01); *A61F 13/64* (2013.01); *A61F 13/84* (2013.01); *A61G 7/0525* (2013.01); *A61G 7/05769* (2013.01); *A61G 7/05776* (2013.01); *A61G 7/07* (2013.01); *A61F 2013/15024* (2013.01); *A61F 2013/15073* (2013.01); *A61F 2013/15154* (2013.01); *A61F 2013/15276* (2013.01); *A61F 2013/15552* (2013.01); *A61F 2013/5147* (2013.01); *A61F 2013/51492* (2013.01); *A61F 2013/8494* (2013.01); *A61G 2203/34* (2013.01); *A61G 2205/60* (2013.01)

(58) Field of Classification Search
USPC .... 128/846, 889, 892; 5/652, 653, 654, 615, 5/713, 715
See application file for complete search history.

(56) References Cited

U.S. PATENT DOCUMENTS

| | | | |
|---|---|---|---|
| 4,799,276 | A | 1/1989 | Kadish |
| 4,873,731 | A | 10/1989 | Williamson et al. |
| 5,092,007 | A | 3/1992 | Hasty et al. |
| 5,815,864 | A | 10/1998 | Sloop |
| 6,273,810 | B1 | 8/2001 | Rhodes, Jr. et al. |
| 6,317,912 | B1 | 11/2001 | Graebe et al. |
| 6,855,158 | B2 | 2/2005 | Stolpmann |
| 7,010,369 | B2 | 3/2006 | Borders et al. |
| 7,017,195 | B2 | 3/2006 | Buckman et al. |
| 7,219,380 | B2 | 5/2007 | Beck et al. |
| 7,883,478 | B2 | 2/2011 | Skinner et al. |
| 8,726,908 | B2 * | 5/2014 | Squitieri .................. A61F 5/34 128/892 |
| 8,757,165 | B2 * | 6/2014 | Squitieri ............... A61F 13/512 128/892 |
| 9,901,491 | B2 * | 2/2018 | Squitieri ........... A61F 13/51474 |
| 9,931,238 | B2 * | 4/2018 | Squitieri ................... A61F 5/32 |
| 10,751,229 | B2 * | 8/2020 | Squitieri ................... A61F 5/32 |
| 2001/0016960 | A1 | 8/2001 | Grabell et al. |
| 2002/0133877 | A1 | 9/2002 | Kuiper et al. |
| 2002/0170117 | A1 | 11/2002 | Flick et al. |
| 2004/0193084 | A1 | 9/2004 | Ravikumar |
| 2004/0222611 | A1 | 11/2004 | Fenwick et al. |
| 2005/0022305 | A1 | 2/2005 | Bieganek et al. |
| 2005/0261656 | A1 | 11/2005 | Garcia et al. |
| 2006/0064800 | A1 | 3/2006 | Freund |
| 2007/0101505 | A1 | 5/2007 | Oprandi et al. |
| 2008/0172797 | A1 | 7/2008 | Niels |
| 2009/0144909 | A1 | 6/2009 | Skinner et al. |
| 2009/0194115 | A1 | 8/2009 | Squitieri |
| 2009/0217460 | A1 | 9/2009 | Bobey et al. |
| 2011/0125330 | A1 | 5/2011 | Huber et al. |
| 2011/0296621 | A1 | 12/2011 | McKenna et al. |
| 2012/0030878 | A1 | 2/2012 | Davenport et al. |
| 2012/0090095 | A1 | 4/2012 | Fraser |
| 2013/0019873 | A1 | 1/2013 | Choi et al. |
| 2013/0255699 | A1 | 10/2013 | Squitieri et al. |
| 2014/0048081 | A1 | 2/2014 | Squitieri et al. |
| 2014/0050680 | A1 | 2/2014 | Garrett et al. |
| 2014/0290670 | A1 | 10/2014 | Squitieri et al. |
| 2015/0164677 | A1 | 6/2015 | Squitieri et al. |

FOREIGN PATENT DOCUMENTS

| | | |
|---|---|---|
| WO | 2004105805 A2 | 12/2004 |
| WO | 2005112855 A2 | 12/2005 |
| WO | 2006131733 A2 | 12/2006 |

* cited by examiner

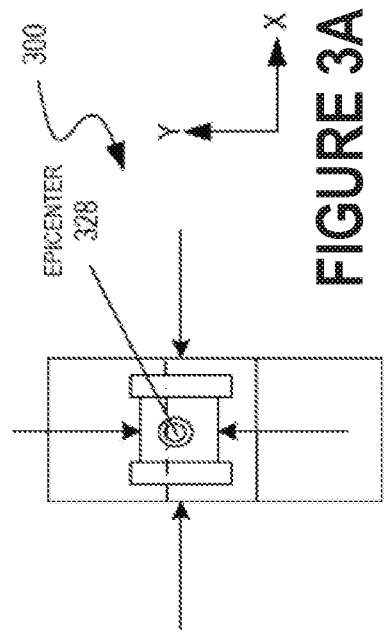
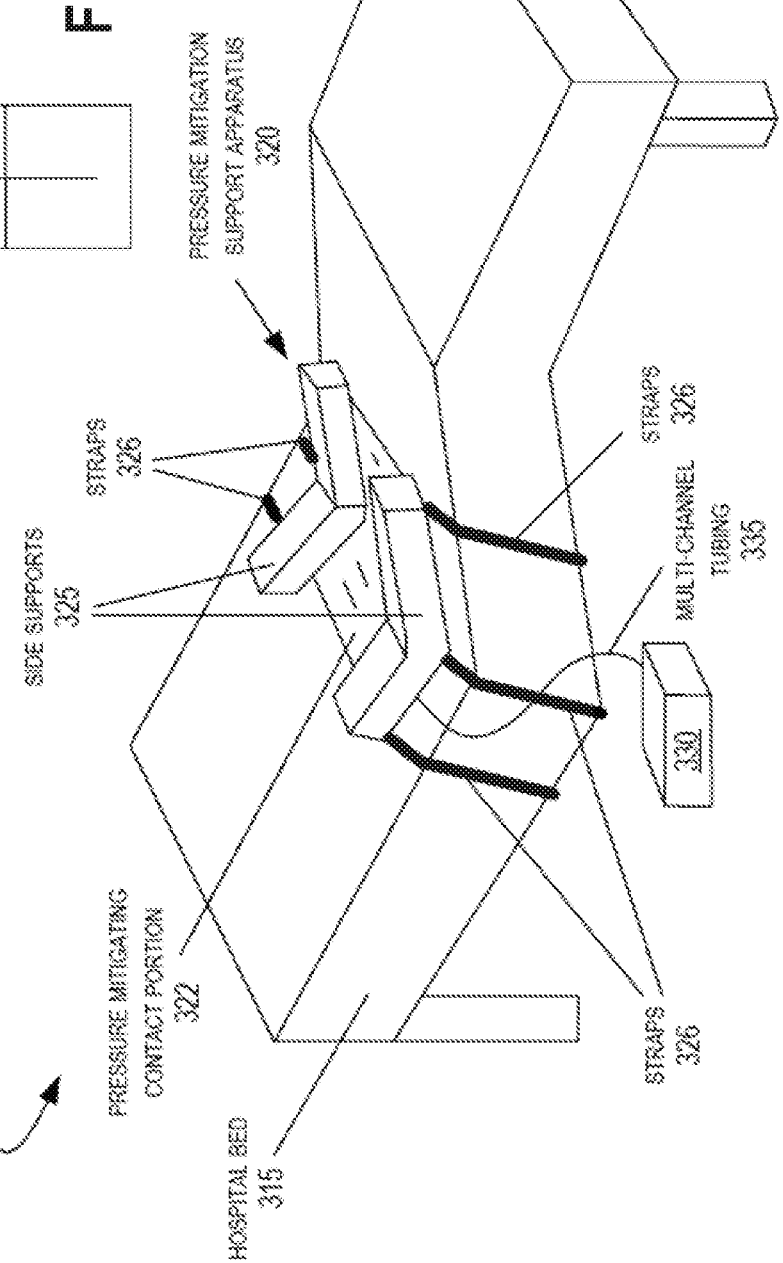

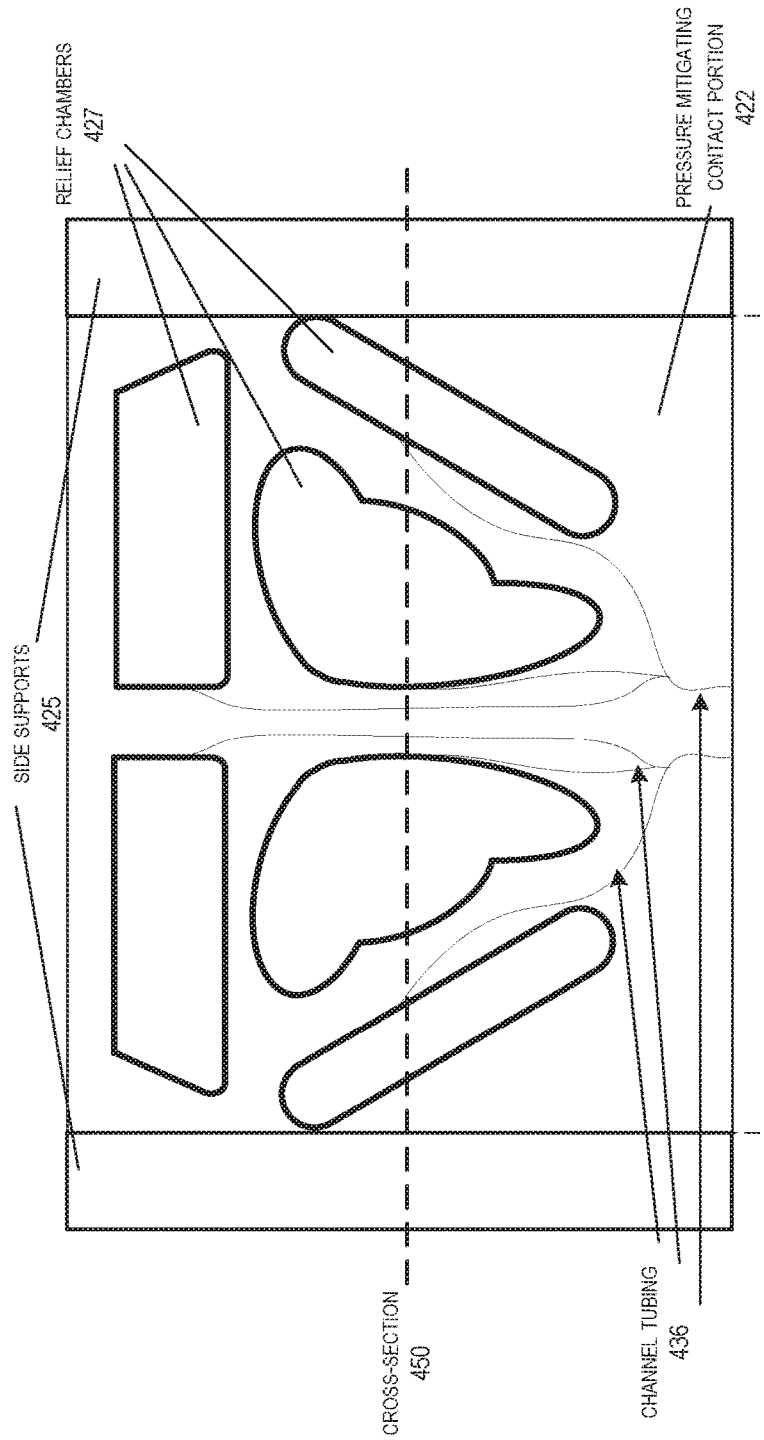
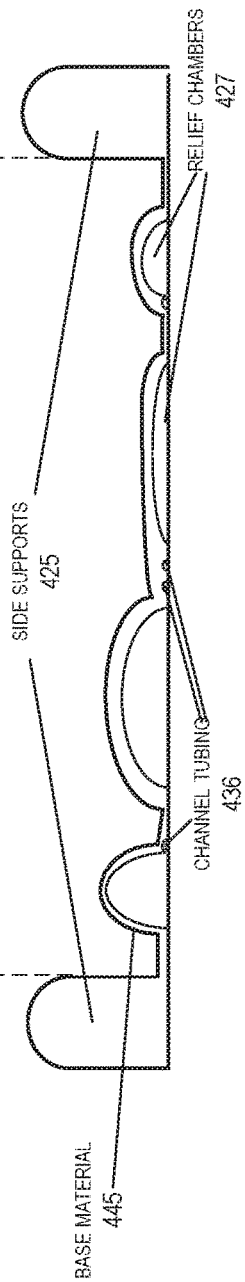
FIGURE 4A
FIGURE 4B

600

610
Determine initial pressure for each of a plurality of independently pressurized chambers built into a therapeutic support surface

612
Determine one or more time settings

614
One or More Pressure Timers Expired for Chamber?

616
Adjust pressure for expired chamber to alternate the pressure on the therapeutic support surface

1102
Diagnose condition affecting a patient

1104
Determine an appropriate treatment regimen for the condition

1106
Promote increased blood flow throughout the human body by varying pressure across a surface of the patient's body

1108
Continue treating the patient in accordance with the conventional treatment regimen

FIGURE 11

NON-INVASIVE PRESSURE-MITIGATION APPARATUSES FOR IMPROVING BLOOD FLOW AND ASSOCIATED SYSTEMS AND METHODS

CROSS-REFERENCE TO RELATED APPLICATIONS

This application is a continuation-in-part of U.S. patent application Ser. No. 15/905,649, filed on Feb. 26, 2018, which is a continuation of U.S. patent application Ser. No. 14/313,570, filed on Jun. 24, 2014 and issued as U.S. Pat. No. 9,901,491 on Feb. 27, 2018, which is a continuation of U.S. patent application Ser. No. 14/063,861, filed on Oct. 25, 2013 and issued as U.S. Pat. No. 8,757,165 on Jun. 24, 2014. U.S. Pat. No. 8,757,165 is a continuation-in-part of U.S. patent application Ser. No. 13/660,429, filed on Oct. 25, 2012, which claims priority to U.S. Provisional Patent Application No. 61/618,936, filed on Apr. 2, 2012. In addition, this application claims priority to U.S. Provisional Application No. 62/647,551, filed on Mar. 23, 2018. Each of these applications is incorporated by reference herein in its their entirety.

This application is related to U.S. Pat. No. 9,931,238, filed May 19, 2014, which is a continuation of U.S. Pat. No. 8,726,908, filed on Oct. 25, 2013. Each of these applications is incorporated by reference herein in its entirety.

TECHNICAL FIELD

The present technology relates generally to non-invasive apparatuses, systems, and methods for mitigating the contact pressure applied to a human body by a support surface.

BACKGROUND

Pressure injuries, sometimes referred to as decubitus ulcers, pressure ulcers, pressure sores, or bedsores, are a frequent but often avoidable complication in many mobility-impaired individuals. These pressure ulcers typically occur as a result of steady pressure in one location along the surface of the human body such as, for example, the sacrum. These pressure ulcers are most common in individuals who are mobility-impaired or immobilized (e.g., in a wheelchair or a bed, or on an operating table) for prolonged periods of time. Oftentimes these patients are older, malnourished, and/or incontinent, all factors predisposing patients to pressure injury formation. Because these patients are often not ambulatory, they may sit or lie for prolonged periods of time in the same position. These individuals often are unable to reposition themselves to alleviate the pressure. Consequently, the pressure on the skin and soft tissue eventually causes ischemia or inadequate blood flow to the area, thereby resulting in breakdown of the skin and tissue damage. Pressure injuries can result in a superficial injury to the skin, or a deeper full-thickness ulcer that exposes underlying tissues and places the individual at risk for infection. The resulting infection may worsen, leading to sepsis, or even death in some cases.

There are many support surfaces on the market for preventing pressure ulcers. However, conventional support surfaces have many deficiencies, including the inability to control the spatial relationship between the patient and the therapeutic surface or contact surface. Consequently, patients using conventional support surfaces may still end up with pressure ulcers or related complications.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure. Furthermore, components may be shown as transparent in certain views for the purpose of illustration, rather than to indicate that the component is necessarily transparent. Any headings provided herein are for convenience only.

FIG. 3A and FIG. 3B depict top and side views, respectively, of an example system for orienting a patient over an anatomy-specific pressure-mitigating support surface on which a patient rests, according to an embodiment.

FIG. 4A and FIG. 4B depict top and cross-sectional views, respectively, of an example pressure mitigation support apparatus, according to an embodiment.

FIG. 6 depicts a flow chart illustrating an example process for coordinated chamber inflation and deflation of a therapeutic surface while the spatial relationship between the patient and the therapeutic surface is controlled by the side-walls of the therapeutic surface.

FIG. 11 is a flow diagram of a process for treating a condition using a pressure-mitigation system in accordance with embodiments of the present technology.

DETAILED DESCRIPTION

Figure 1:
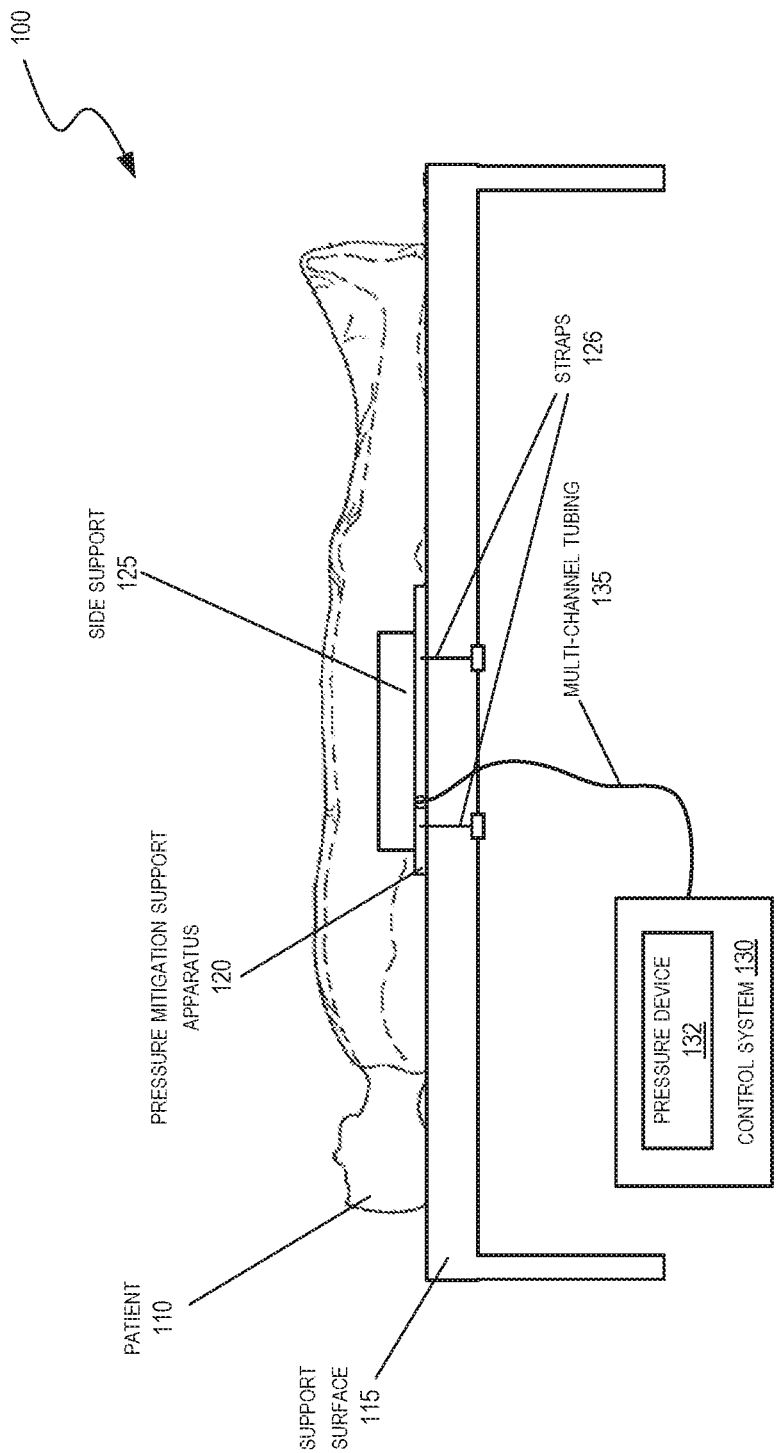
FIG. 1 depicts a side view of an example system for orienting a patient over an anatomy-specific pressure-mitigating contact surface on which the patient rests, according to an embodiment.

Pressure injuries (also referred to as "ulcers") are localized regions of damage to the skin and/or underlying tissue that result from contact pressure (or simply "pressure") on the corresponding anatomical region of the body. Pressure injuries often form over bony prominences, such as the skin and soft tissue overlying the sacrum, coccyx, heels, or hips. However, other sites (e.g., elbows, knees, ankles, shoulders, abdomen, back, or cranium) may also be affected. Generally, pressure injuries occur when pressure is applied to blood vessels in soft tissue, which at least partially obstructs blood flow to the soft tissue and can lead to ischemia at the pressure site for an extended duration (e.g., when the pressure exceeds the capillary filling pressure). Therefore, pressure injuries often occur in humans who are mobility impaired, immobilized, or sedentary for prolonged periods of times. When pressure is relieved from the site of the pressure injury, the body rushes blood to that region to re-perfuse the area. The sudden reperfusion of the damaged, previously ischemic region has been shown to cause a reperfusion injury, characterized by a profound inflammatory response involving the release of proinflammatory mediators. This pathogenic process can actually worsen the original pressure injury and may spread through the blood stream beyond the site of the initial ischemic insult to cause a systemic inflammatory response. The presence of proinflammatory mediators has been shown to exacerbate existing conditions or trigger additional ailments, thereby slowing patient recovery. Moreover, patient recovery time can be prolonged by numerous factors often associated with patients prone to pressure injuries, such as old age, immobility, preexisting medical conditions (e.g., arteriosclerosis, diabetes, or infection), smoking, and/or medications (e.g., anti-inflammatory drugs). Thus, preventing or reducing pressure injury formation and reducing proinflammatory mediators can enhance and expedite many treatment processes for patients, especially those who are mobility-impaired during the course of treatment.

Introduced here, therefore, are apparatuses and systems for mitigating the pressure applied to a human body by the surface of an object, such as a chair, bed, table, or other support surface. A non-invasive pressure-mitigation or perfusion enhancement apparatus (also referred to as a "pressure-mitigation device," a "pressure-mitigation pad," or a "perfusion enhancement apparatus") can include a series of chambers (also referred to as "cells") whose pressure can be individually varied. When placed between a patient and a contact surface (e.g., a bed or a chair), the pressure-mitigation apparatus can vary the pressure on one or more specific anatomical regions of the patient by controllably inflating one or more chambers, deflating one or more chambers, or any combination thereof.

Specific details of several embodiments of the present technology are described herein with reference to FIGS. 1-12. Although many of the embodiments are described with respect to apparatuses, systems, and methods for alleviating the pressure applied to a human body in a supine position by a contact surface, other embodiments in addition to those described herein are within the scope of the present technology. For example, at least some embodiments of the present technology may be useful for alleviating the pressure applied to a human body in a sitting position. In such embodiments, the chambers of the pressure-mitigation apparatus may be inflated in a different order, with different pressures, for different durations, etc.

It should be noted that other embodiments in addition to those disclosed herein are within the scope of the present technology. For example, components, configurations, and/or procedures shown or described with respect to one embodiment can be combined with or replace the components, configurations, and/or procedures described in other embodiments. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein, and that these and other embodiments can be without several of the configurations, components, and/or procedures shown or described herein without deviating from the present technology.

Selected Embodiments of Pressure-Mitigation Apparatuses

Embodiments of the present disclosure include examples of systems, methods, and apparatuses for the prevention and treatment of pressure injuries. In particular, the pressure injury prevention systems and/or apparatuses (also referred to as "perfusion enhancement systems") disclosed herein prevent or otherwise mitigate pressure injuries by actively orienting a patient over an anatomy-specific pressure-mitigating contact surface on which the patient rests. A pressure-mitigating contact portion of the contact surface includes a plurality of independently pressurized chambers configured in a specific geometric pattern that is designed to mitigate contact pressure between a support surface (e.g., bed or chair) and a specific anatomic region of a patient's body when the specific anatomic region of the patient's body is oriented over an epicenter of the geometric pattern.

In one embodiment, the pressure injury prevention systems and/or apparatuses control pressure beneath specific anatomic locations of the patient for specific durations in order to move pressure points around the anatomy in a precise manner such that specific portions of the anatomy (e.g., tissue adjacent bony prominences) have zero pressure applied for predetermined periods of time. This continuous or intermittent relocation of the pressure point(s) avoids vascular compression for sustained periods of time and, therefore, inhibits ischemia and ultimately reduces the incidence of pressure injuries. Thus, the pressure injury prevention systems and/or apparatuses make it possible to increase and decrease the pressure beneath a patient at specific locations for set periods of time in order to maximize the potential therapeutic benefits of a therapeutic surface.

In one embodiment, the pressure injury prevention systems and/or apparatuses are specifically designed for mitigating pressure and/or otherwise preventing prolonged vasocompression to avoid ischemia, reperfusion injury, and the associated health implications (e.g., pressure injuries) in the sacral area or region of the human anatomy. This is unlike prior art surfaces or overlays that are typically placed beneath the entire length of the patient and do not function based on being uniquely oriented beneath a specific location (or anatomic region) of the patient.

In one embodiment, the geometric pattern is designed and/or shaped according to general human anatomy and/or the individual patient's specific anatomy. For example, if the pressure injury prevention systems and/or apparatuses are designed to mitigate contact pressure between a support surface and the patient's sacral region then the independently pressurized chambers are designed in specific shapes to fit to the patient's pelvic bones, the gluteus muscles, and/or the sacral arties. In one embodiment, the geometric pattern is symmetric and non-repeating in nature.

In one embodiment, the device's patient contact portion is designed to actively orient the patient over the support surface portion in a way that allows an apparatus to "know" for the first time the location of the patient on that device. The apparatus is designed to take advantage of this knowledge regarding the location of the patient to more effectively mitigate and systematically rotate the damaging pressure that leads to the formation of pressure injuries.

In one embodiment, the apparatuses described herein comprise mattress overlay devices. The described overly devices differ from the prior art mattress overlays that cover the full surface of the bed. Further, the prior art mattress overlays typically have a repeating pattern throughout and allow a patient to freely move about over the entire surface of the bed. Conversely, the apparatuses described herein are anatomy-specific and may only be the size of the patient's anatomy that makes contact with the apparatus. Accordingly, the disclosed systems, methods, and apparatuses take advantage of the inherent knowledge of the patient's location on the anatomy-specific pressure-mitigating contact surface to systematically rotate and/or otherwise alternate the damaging pressure that leads to the formation of pressure.

In one embodiment, the patient can be actively oriented over an anatomy-specific pressure-mitigating contact surface by controlling the spatial relationship between the patient and the contact surface through the use of one or more side support portions. In some embodiments, the side support portions may be inflatable. In other embodiments, the side support portions are fixed. In the former case, the side support portions may be independently inflated with any appropriate gas or liquid. The inflation of the side support portions is independent of the pressurized relief chambers on the pressure-mitigating contact portion. In some embodiments, the side support portions may be inflated independent of each other in order to properly orient the patient. This can be based on the actual pressure in a side support portion versus an expected pressure in that side support portion as determined by a control device. Alternatively or additionally, one or more sensors can be built into the side support portions that identify discrepancies in the ideal position of the patient on the anatomy-specific pressure-mitigating contact surface and attempt to adjust the patient accordingly (e.g., by independently adjusting the pressure in the side support portions).

In one embodiment, the pressure in the side support portions is fixed. In this case, the fixed side support portions may be fixed using a liquid, a gas, and/or a solid. In the case where a solid is used, Styrofoam, and/or any "cushion like" materials can be utilized. The side support portions may be elevated in height above the anatomy-specific pressure-mitigating contact surface in order to prevent a patient from lateral movement (i.e., movement along the x-axis). For example, the side support portions may be elevated, when inflated, two to three inches in vertical height above the average surface height of the pressure-mitigating contact portion.

Further, to prevent movement along the y-axis the anatomy-specific pressure-mitigating contact surface may be designed such that a specific portion of the contact surface is aligned over the surface of a V formed in a patient's hospital bed. In one embodiment, the side support portions may be attached to the sides of a pressure-mitigating contact portion. In one embodiment, the side support portions may be configured with a recess configured to accommodate a patient's elbow. The recess that accommodates the patient's elbow results in a more comfortable device that offloads pressure over the elbow of the patient.

In one embodiment, the design of the pressure injury prevention systems and/or apparatuses disclosed herein take into account and/or control for various factors that influence functionality and/or effectiveness of the pressure injury prevention systems and/or apparatuses. For example, the systems and/or apparatuses may take time, space, patient weight, patient position, real-time interface pressure, existing conditions (e.g., existing pressure injuries), and/or human anatomy into account in the prevention of pressure injuries.

In one embodiment, the systems and/or apparatuses may be employed as a mattress overlay. For example, the overlay device or apparatus could be deployed on any mattress, chair, or other support surface. Alternatively or additionally, the systems and/or apparatuses may be incorporated into the design of a mattress.

In one embodiment, the surface area of the pressure relief surface is designed to match (or be less than) the size of the patient's surface anatomy in the region of contact made between the patient's anatomic region and the device. For example, the size of the pressure relief surface may be the size of the patient's surface anatomy in the region of contact made between the patient's sacral region and the pressure mitigation support apparatus. Further, the pressure relief surface may be contoured to fit the surface topography of the patient's surface anatomy in the region of contact made between the patient's sacral region and the pressure mitigation support apparatus. The internal anatomy is considered in the pattern—not the height—of the relief chamber design.

In one embodiment, the pressure relief apparatus is designed such that no portion of the independently pressurized relief chambers of the surface area of the pressure relief surface in contact with the patient is left uncovered by the patient. That is, the independently pressurized relief chambers in contact with the patient can be smaller than or equal to but not larger than the area of contact with the patient. This feature improves performance of the pressure relief apparatuses described herein. Conversely, with prior art standard alternating pressure overlays, the pressure relieving air cells are much larger than the contact area with the patient and therefore the air cells are only partially covered by of the patient. Thus, with prior art designs, the uncovered portions of the pressure relieving air cells act as a reservoir "sink" for the inflated air and minimize the lifting capabilities of these surfaces that are needed to create areas of low pressure fundamental to the optimal functioning of such a device.

In one embodiment, the independently pressurized relief chambers of the pressure relief apparatus are unique in that the entirety of the surface area of the independently pressurized relief chambers are in contact with the patient such that no portion of the independently pressurized relief chambers is left uncovered by the user. Therefore, in this embodiment, the individual independently pressurized relief chambers of the pressure relief apparatus can be smaller than or equal to but not larger than the area of contact with the patient. This feature can improve performance of the pressure relief apparatus. In the case of prior art standard alternating pressure overlays, the pressure relieving air cells are much larger than the contact area with the patient and therefore the air cells are only partially covered by of the patient. Thus, with prior art designs, the uncovered portions of the pressure relieving air cells act as a reservoir "sink" for the inflated air and minimize the lifting capabilities of these surfaces that are needed to create areas of low pressure fundamental to the optimal functioning of such a device.

In one embodiment, the systems and/or apparatuses can be employed as a mattress overlay and/or incorporated into the design of a mattress itself. The overlay can be deployed on any mattress or chair. The design of the pressure mitigation surface portion of the overlay portion of the device takes into account multiple factors. These factors include patient comfort, patient anatomy, patient position (seated, flat, 30 degrees head up), and anatomic locations with a propensity to develop pressure injuries.

It is appreciated that the term "patient" as used herein can include any individuals, users or persons that are mobility impaired for prolonged periods of time and thus susceptible to pressure injuries.

FIG. 1 depicts a side view of an example system 100 for orienting a patient over an anatomy-specific pressure-mitigating contact surface on which the patient rests, according to an embodiment. The example system 100 includes a patient 110, a support surface 115, a pressure mitigation support apparatus 120 and a control device 130. A more detailed example of a specific pressure mitigation support apparatus (e.g., partial body alternating contact pressure mattress overlay device) is shown and discussed in greater detail with respect to FIG. 2.

In the example of FIG. 1, the pressure mitigation support apparatus 120 is comprised of two elevated side support portions 125, a pressure-mitigating contact portion (shown in FIG. 2), and straps 126. The pressure-mitigating contact portion includes a plurality of independently pressurized relief chambers interconnected on a base material. As described herein, the independently pressurized relief chambers are configured in a geometric pattern that mitigates contact pressure between the support surface 115 and a specific anatomic region of a patient's body when the specific anatomic region of the patient's body is oriented over an epicenter of the geometric pattern. The support surface 115 may be a hospital bed, a mattress, and/or other surface on which a patient is positioned in at least partially supine position.

The elevated side support portions 125 are configured to actively orient the specific anatomic region of the patient's body over the epicenter of the geometric pattern. As shown, the specific anatomic region of the patient's body is the sacral region. However, it is appreciated that the specific anatomic region can be any specific region of the patient's body that is susceptible to pressure injuries (e.g., ulcers). The side support portions 125 are configured so as to be ergonomically correct. For example, the side support portions 125 may be configured with a recess to accommodate the patient's elbows in some embodiments resulting in a more comfortable apparatus that off loads pressure over the elbow of the patient.

The elevated side support portions 125 can be significantly larger in size as compared to the size of the pressure relief surface air cells. As a result, the elevated side support portions 125 create a barrier that keeps a patient from moving laterally or sideways off of the anatomy-specific pressure-mitigating contact surface. In one embodiment, the elevated side support portions 125 may be on average at least 2-3 inches taller in vertical height after inflation as compared to the average height of the inflated (or pressurized) pressure-mitigating contact portion. Because the elevated side support portions 125 are larger and do not go underneath the patient, but instead straddle the sides of the patient, the elevated side support portions 125 act to hold and position the patient on top of the anatomy-specific pressure-mitigating contact surface.

The straps 126 are configured to secure the pressure mitigation support apparatus to the support surface.

In one embodiment, inner side walls of the elevated side support portions 125, on initial inflation of higher pressure, form a firm surface at a steep angle of orientation with respect to the patient on the pressure mitigation support apparatus 120. For example, the inner side walls may be on a plane of 115 degrees plus or minus 25 degrees from the plane of the pressure mitigation support apparatus 120. These steep inner side walls create a steeply angled side wall down which the patient, when positioned inappropriately off to one side or another, will slide down toward an epicenter of a geometric pattern formed on the pressure mitigation support apparatus 120. Thus, inflation or pressurization of the elevated side support portions 125 actively forces the patient into a position ideal for the mitigation of pressure by orienting the user in the correct position over the pressure mitigation support apparatus 120. As a result, the patient's anatomy will be correctly aligned with respect to the x-axis.

Once the initial inflation cycle has finished and the user is properly positioned, the internal pressures of the elevated side support portions 125 may decrease to a lower pressure to increase comfort and prevent excessive force against the lateral aspect of the patient. Ideally, a caregiver of the patient will be present during the initial positioning of the patient over the pressure mitigation support apparatus 120 to ensure proper positioning of the patient by the elevated side support portions 125.

In one embodiment, the elevated side support portions 125 comprise steeply angled side walls. For example, the walls may be angled such that the inner aspect of the elevated side support portions 125 which contact the user on the lateral aspects of each hip/thigh region simultaneously will form an obtuse angle of between 90 to 145 degrees with respect to the plane of the pressure mitigation support apparatus 120 (i.e., a pressure-mitigating contact portion). The elevated side support portions 125 may be connected by pressure channels (e.g., air channels).

In one embodiment, the elevated side support portions 125 are inflated and deflated in series together. Thus, like the independently pressurized relief chambers, the air pressure in the elevated side support portions 125 can be controlled by the control device 130. Alternatively or additionally, each side support portion of the elevated side support portions 125 can be controlled by a unique control device and/or pump within the pump housing. The pressures within the elevated side support portions 125 can be determined based on pre-set parameters of the individual pump cycle as determined on an individual patient specific basis (e.g., individual parameters based on the weight, existing pressure injuries, and/or position of the patient).

In one embodiment, there can be one or more air (or pressure) channels (not shown) between the elevated side support portions 125. In some cases, the air channels can be redundant. Redundancy of air channels allows for even distribution of air (or other pressure) between the elevated side support portions 125. For example, one air channel may traverse the outside (or perimeter) of the pressure mitigation support apparatus 120 to the top of the apparatus while a second air channel traverse the outside of the pressure mitigation support apparatus 120 a lower edge of the apparatus. This configuration or arrangement creates a closed loop circle around the pressure mitigation support apparatus 120 which allows air to pass unobstructed from the pump into a first one of the elevated side support portions 125 through the connecting air channels and into a second one of the elevated side support portions 125 without the weight of the patient blocking both channels simultaneously as this is physically improbable with the redundant configuration described herein.

In one embodiment, the pressure channels can flare out slightly at the point of entry into the elevated side support portions 125 so as to reduce the likelihood of kinking or otherwise disturbing the inflation and/or pressurization of the pressure channels.

In one embodiment, the pressure mitigation support apparatus 120 can have an additional elevated side support portion 125 that is positioned between the legs of a patient along the lower aspect of the pressure mitigation support apparatus 120 (not shown). This additional elevated side support portion 125 can prevent a patient from migration toward the foot of the bed in the y-axis.

In one embodiment, the elevated side support portions 125 function much like the side arms of a chair which has a seat portion that is the same size as the "seat" of the user (e.g., a chair that is too small for a user). These side arms allow only a small lateral position shift of the user. As is the case with the pressure mitigation support apparatus 120, this minimal lateral motion is not great enough to allow the user to displace their location off of the pressure mitigation support apparatus 120 to a degree that will render the pressure relief characteristics less effective.

The control system 130 is configured to regulate the pressure of each of the independently pressurized relief chambers via a pressure device 132 (e.g., air pump) and multi-channel tubing 135. For example, the independently pressurized relief chambers may be controlled in a specific pattern to preserve blood flow by reducing contact pressure in specific, varying locations when inflated (pressurized) and deflated (depressurized) in a coordinated fashion that is controlled by the control device 130. The multi-channel tubing 135 connects the pressure mitigation support apparatus 120 with the air pump control system 130. One or more connectors (not shown) may be used to make these connections.

The control system 130 is configured to be programmed by a patient, healthcare personnel, the patient, etc. In one embodiment, the control system 130 can be programmed on a patient-specific basis to manage and mitigate pressure on one or more existing pressure injuries that are currently present on a patient in a specific anatomic location. As the geometry of the design is specific to the patient's anatomy, the location of the pressure injuries on the patient can be entered into the computer controlled pump and the ideal pressure time cycle optimized for healing the pressure injury in that specified anatomic location. For example, if a patient has a pressure injury in the typical location over the sacral bone centrally, the cycle will preferentially drop the pressures in this location and shorten the duration of pressure delivered to this location in order to promote healing of the pressure injury. Similarly, if the pressure injury is located over a specific ischial tuberosity, right or left, the pressure can be preferentially relieved in this location as the independently pressurized chambers are specifically designed to fit the underlying anatomy and each region of concern is able to be controlled specifically.

In one embodiment, the multi-channel tubing 135 comprises multi-lumen tubing to control pressure at different chambers of the plurality of independently pressurized chambers. Multi Lumen tubing has multiple channels running through its profile. Multi Lumen tubing has a variable Outer Diameter (OD), numerous custom Inner Diameters (ID's), and various wall thicknesses. The tubing can be in a number shapes; circular, oval, triangular, square, crescent, etc.

In one embodiment, the control system 130 may comprise a computer-controlled multi-channel air pump. The control system 130 may have a number of programmable settings and memory to remember preferences. For example, the control system 130 may regulate the pressure beneath one or more specific anatomic location(s) based on the weight of the patient 110, which may be programmed by an individual (e.g., the patient 110 or a medical professional) via an interface generated by the control system 130. Further, in some embodiments, the control system 130 can control pressure beneath one or more specific anatomic location(s) for specified durations in order to maximize blood flow and reduce pressure. The specified durations can be programmable. For example, the control system 130 can control the pressure in each of the individual pressurized relief chambers of the pressure mitigation support apparatus 120 such that the pressure in any chamber changes or is modified after a specified period of time. In this way, no part of the patient's body is left in contact with the pressure mitigation support apparatus 120 for more than a period of time. The period of time is programmable and may be based on pre-programmed settings or customizable by the patient and/or a health care professional.

Unlike some alternating pressure support surfaces, the adjustable side walls 125 fix the relationship between the patient and the pressure mitigation support apparatus 120. As a result, the pressure mitigation support apparatus 120 can reliably reduce pressure in a concerted or consistent fashion for any specific region of the patient's body in jeopardy of developing a pressure injury because the patient is not free to move about over the pressure mitigation support apparatus 120. Further, unlike products with side support surfaces such as, for example, supports to keep patients from falling off a large overlay support surface (i.e., a mattress overlay) or the supports on a typical hospital bed, the side supports 125 are customizable to the patient. For example, the side walls 125 may be inflatable (pressurized) to fit to the patient and keep the patient in the correct position (i.e., keep the anatomic region of the patient's body oriented over an epicenter of the geometric pattern). The pressure mitigation support apparatus 120 presented herein is designed with a geometry that requires the patient be properly held in position on the surface in order for the design to effectively mitigate the pressure beneath the patient and maximize blood flow to the tissues at risk for ulceration.

In one embodiment, the side supports 125 will contact the patient gently on the lateral aspect of both hips simultaneously in order to actively orient the patient in the correct orientation on the surface. The pressure mitigation support apparatus 120 can be customized specifically to each individual patient in order to be effective at pressure injury reduction. As will be appreciated, this design is quite different from the support surfaces that utilize side walls as a safety barrier to prevent patients from moving off or falling off the surface support as the patient is free to move about over these surfaces laterally between the sidewalls that are typically as wide apart as a standard hospital bed. These current products do not require the person to be in a precise location on the surface as opposed to the patient-orienting surface described here.

Being anatomy (or location) specific beneath the patient, allows the apparatus to evenly distribute and rotate pressure from one known location to another ensuring that no one area is under the damaging effects of constant pressure for a prolonged period of time that could lead to cell death from ischemia that leads to tissue breakdown and pressure injury formation. Prior art support surfaces which allow a patient to move freely over the support surface cannot reliably rotate pressure from a specific area to another and therefore are limited in their ability to prevent pressure injuries as compared to the systems and apparatuses described herein.

Ideally, patients are positioned head up at 30 degrees in bed to prevent aspiration pneumonia and to optimally offload the patient's weight off of the sacrum and ischial tuberosities. This is also the ideal bed position to ensure optimal function of the apparatuses disclosed herein. However, in the event that a patient is positioned flat in bed at 0 degrees as shown is the case of the intubated, anesthetized and hypotensive ICU patient (and as shown in FIG. 1), it will be necessary to confirm ideal patient position over the device without the benefit of y-axis orientation control achieved by placing the bed at 30 degrees head up (discussed in greater detail with reference to FIG. 3).

In one embodiment X- and/or Y-axis orientation control can be alternatively or additionally achieved through the use of a radio frequency (RF) antenna device. For example, as an additional measure to confirm patient location over the epicenter of our device, an RF antenna can be incorporated into the pressure-relieving surface. A thin flexible RFID tag/label may be placed on the patient's sacrum using a biologic dressing material. When in the proper orientation, the RFID tag will be detected by the antennae and a signal light and sound will confirm the correct position without needing to look beneath the patient and inspect correct location by direct vision. The indicator signal will display the correct direction in which to move the patient should reorientation be required by the staff to ensure the mobility impaired patient (e.g., a patient that is immobile, bed-bound, etc.) is correctly positioned over the device to maximize pressure redistribution and pressure rotation/relocation.

Figure 2:
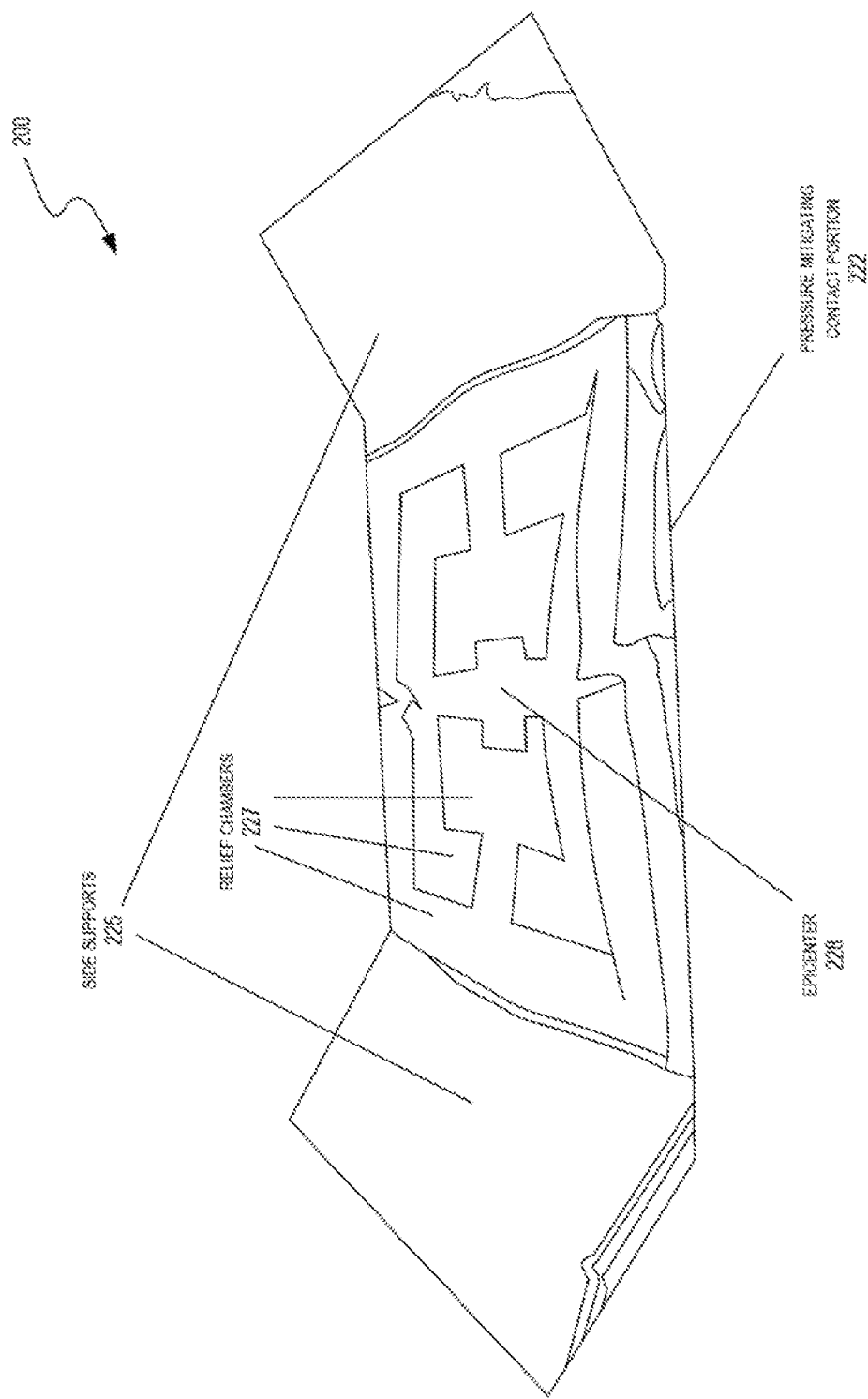
FIG. 2 depicts an example pressure mitigation support apparatus, according to an embodiment.

FIG. 2 depicts an example pressure mitigation support apparatus 200, according to an embodiment. The pressure mitigation support apparatus 200 includes side supports 225 and a pressure-mitigating contact portion 222. The pressure-mitigating contact portion 222 includes a plurality of independently pressurized relief chambers 227. The independently pressurized relief chambers 227 are configured in a specific geometric pattern that mitigates contact pressure between a support surface and a specific anatomic region of the patient's body when the specific anatomic region of the patient's body is oriented over an epicenter of the geometric pattern.

As shown in the example of FIG. 2, the epicenter may be a central point of the pressure mitigation support apparatus, however the epicenter need not be the central point of the apparatus. For example, the epicenter may not be the central point if the pressure mitigation support apparatus is not symmetric (or even if it is). In some embodiments, the epicenter is a portion of the device that is specifically designed to match up with an epicenter of the specific anatomic region of the patient's body (e.g., the sacral bone when the specific anatomic region is the sacral region). In one or more embodiments, the epicenter will be marked so that a patient and/or a caregiver (e.g., nurse) can easily identify the epicenter of the apparatus.

In this example, the pressure mitigation support apparatus 200 includes a plurality of independently pressurized relief chambers 227 that are configured in a specific "C-shaped" geometric pattern that effectively mitigates and/or otherwise relieves contact pressure between a support surface and a sacral region of a patient's body when the pressure in the plurality of independently pressured relief chambers 227 is alternated. The anatomy specific "C-shaped" geometric design allows the geometric pattern to properly align with the patient's anatomy resulting in superior redistribution and relocation of pressure as compared to prior art support surfaces.

The geometric pattern(s) described herein are specifically designed to coincide with the internal anatomy of the sacral region. For example, the geometric pattern of independently pressurized relief chambers 227 conforms to a shape based on the internal anatomy (muscle, bone, vessel) in order to maximize the pressure-relieving properties of the apparatus. As a result, pressure relief can be provided in specific areas of the sacral region that are most prone to pressure injury formation, namely over the bony prominences—the sacrum and ischial tuberosities. The pattern of the apparatus is therefore symmetric and non-repeating in nature. This is different from prior art support surfaces that typically employ repeating patterns over a large surface area of an entire bed mattress. The functionality of these prior art surfaces does not require knowledge of the location of a patient. That is, with prior art surfaces there is no benefit for the patient being in one location verses another. Accordingly, the prior art surfaces are less effective and less accurate than the systems and/or apparatuses disclosed herein.

In the example of FIG. 2, the geometric pattern illustrates two lateral relief chambers forming "C" shapes facing each other around a central circular relief chamber which is the size of the sacral bone and positioned directly over the sacral bone. The central circular relief chamber is designed to fit the area of skin just at the top of the gluteal fold that overlies the sacral bony prominence which is the area at greatest risk for pressure injury formation.

In addition to the ability to directly relieving central pressure, the device is designed to intermittently relieve pressure just lateral to this central area. It is in this lateral region that the blood supply to the central region is located. The major blood supply via a named artery to the skin overlying the central sacral area runs in a course from deep within the pelvis around the lateral aspect of the sacral bone and travels to the skin overlying the sacrum centrally. Lateral pressure directly beneath the C shape regions which overlies the feeding arterial blood supply to the central sacral region will lead to ulceration centrally over the sacral bony prominence. The C shapes are located directly over the superior gluteal arteries, the vascular blood supply to the skin overlying the sacral bone.

A right and left superior gluteal artery run beneath the right and left C shapes respectively. By deflating the relief chamber that comprises the right C shape while the central air cell and the left C shaped relief chamber remain inflated, the pressure over the right superior gluteal artery is relieved and blood flow is optimized through the right superior gluteal artery to skin overlying the central area over the sacral bone. Similarly, pressure can be relieved over the left superior gluteal artery by performing a similar process with respect to the C-shaped air cell over the left superior gluteal artery. Pressure is rotated from one area to another as a result. The harmful effects of constant pressure in one location for a prolonged period of time which can lead to pressure injury formation are therefore avoided. These air cells are intertwined so that any individual air cell may be deflated and the other air cells that remain inflated will support the area defined by the now un-inflated air cell such that an area of low pressure is created in the area beneath the un-inflated air cell.

In one embodiment, the specific pressure mitigation support apparatus 200 may be a partial body alternating contact pressure mattress overlay device as shown and discussed in greater detail with respect to FIG. 3A and FIG. 3B. The pressure mitigation support apparatus 200 may be the pressure mitigation support apparatus 120 of FIG. 1; although alternative configurations are possible.

In the example of FIG. 2, the side supports 225 control the spatial relationship between the patient and the pressure-mitigating contact portion 222. As discussed, the geometric pattern of the pressure-mitigating contact portion 222 is designed to reduce constant pressure on the patient in the same place. In one embodiment, the side supports 225 may not be inflatable but fixed. In one embodiment, side supports 225 are disposed on each side of the support surface 200 to support patients of variable hip width. Further, in some embodiments, the side supports 225 may be decreasing in width from the outermost wall to the innermost wall. It is appreciated that a geometric pattern is shown for simplicity. The pressure-mitigating contact portion 222 may include a variety of different patterns and/or designs and sizes. Further, it is appreciated that the specific pressure mitigation support apparatus 200 can be designed to reduce pressure for specific regions or portions of a patient's body and/or for a patient's entire body in some instances.

A control system such as, for example, the control system 130 of FIG. 1 individually controls the pressure in each of the independently pressurized relief chambers. The pressure and length of time each air cell is at a specific pressure will be determined by an algorithm within the software program. In order to maximize the efficacy of the system, the specific pressures and timing cycles that will be utilized are patient-specific. The specific program (time/pressure cycle) specified for an individual patient may be determined by the specific patient's characteristics and/or factors that are entered into the pump controller program. This data is used to call for the optimal program for that patient. Possible characteristics and/or factors can include, but are not limited to, the patient's weight, the type of surface upon which the apparatus or overlay rests (e.g., bed, stretcher, air mattress, etc.), the patient position (flat in bed, bed at 30 degrees, bed at 45 degrees, bed at 90 degrees, sitting in chair, etc.), and/or the location of preexisting pressure injuries. These characteristics and/or factors may be used to determine the pressure for the independently pressurized relief chambers over a period of time (e.g., the alternating pressure or the pressures needed to effectively redistribute and relocate pressure within a specific anatomic area).

In one embodiment, real-time (or near real-time) feedback from the independently pressurized relief chambers will allow the pump to adjust the pressure within each relief chamber towards the desired set pressure for each air cell at each phase of the cycle. Each relief chamber may be set to a specific pressure for a specific length of time. The cycles of each chamber will be coordinated with respect to all other chambers creating a coordination of inflations and deflations of the entire group of pressure relief chambers to maximize pressure redistribution and relief within the apparatus. It is appreciated that there are a finite number of cycle patterns that can achieve the desired result based on the physical constraints dictated by the human anatomy, the size of the sacral area, and the size that the air cells need to be in order to be effective at pressure relief yet comfortable and not prone to mal-align the long axis of the patient's spine if they are too tall in height.

The physiologic pressure around 32 mmHg is the ideal threshold below which pressure ulceration is less likely to occur. Given this ideal pressure target of 32 mmHg, the apparatus includes an ideal size of 2-3 inches for the pressure relief chambers in a partial body overlay that will create the required wall tension of the surface of these air cells to effectively redistribute high pressure points without causing mal-alignment of the long axis of the patient's spine. Additionally, in some embodiments, the difference in height between adjacent pressure relief chambers is not more than 1 inch in vertical height after inflation so as not to create a surface that is uncomfortable to the patient.

The ideal internal pressures that are optimal in conjunction with the identified ideal shapes of the pressure-relieving portion of the device or apparatus, namely, given the shape and design of the pressure relief surface (or pressure-mitigating contact portion), using pressures within the central pressure relief chamber that are on average 10 mmHg higher than the two lateral pressure relief chambers will produce, include optimal redistribution of interface pressure between the patient and the device.

In one embodiment, the pressure mitigation support apparatus 200 may be constructed of various materials. For example, material used in construction of the inflatable or patient contact portion of the pressure mitigation support apparatus 200 may be determined by the nature of the contact. If the pressure mitigation support apparatus 200 is in direct contact with skin a soft, low sheer, breathable fabric is ideal. This fabric will have an impervious lining like, for example, polyurethane, etc. that is air tight and used to create the air tight chambers. The materials may be reusable and sterilizable. Conversely, if the pressure mitigation support apparatus 200 is underneath a protective cover or bed sheet, then the inflatable device can be made of an impervious flexible material like polyurethane. This is ideal for a multi-patient patient as it is easily washable and sterilized.

FIG. 3A and FIG. 3B depict top and side views, respectively, of an example system 300 for orienting a patient over an anatomy-specific pressure-mitigating support surface 320 on which a patient (not shown) rests, according to an embodiment. In this example, the anatomy-specific pressure-mitigating support surface 320 is used in conjunction with a typical hospital bed 315 (i.e., support surface) to control the spatial relationship between the patient and the hospital bed. A control system 330 alternates pressure in the chambers of the anatomy-specific pressure mitigating support surface 320. The control system 330 may be the control system 130 of FIG. 1, although alternative configurations are possible.

More specifically, in the examples of FIG. 3A and FIG. 3B the support device 320 is placed on or otherwise secured to a standard hospital bed 315 that can maintain a 30 degree incline position. The epicenter of the device 328 is aligned over the break in the bed so that when a patient is seated on the device the side supports 325 keep the person centered laterally (e.g., along the x-axis or from side to side). In this configuration, the bed is in a 30 degree "V" shape position that will keep the person from moving toward the head or foot of the bed. This creates a centering of the patient over the surface in both the east-west (between the side walls) and north-south (between the head and leg elevations) directions.

The epicenter 328 of the pressure relieving surface of the apparatus is designed to contact the sacrum of the patient at the top of the gluteal fold. This is the area of greatest incidence of pressure injuries in bed bound individuals. The apparatus is specifically and uniquely shaped to protect this portion of the patient anatomy as it represents the center of the pressure relief surface around which the design is constructed. Conversely, as previously discussed, the repeating patterns of prior art surface designs at are not anatomy specific. The epicenter 328 is designed to be placed and fixed on a support surface (e.g., hospital bed) such that the epicenter 328 is located and/or otherwise oriented over the break (or "V") in the bed.

In one embodiment, the epicenter 328 of the apparatus is readily identified by its visual characteristics and marked by a central 0.5 inch weld at the very center of the pattern. This central half inch circle is visually aligned with the joint in the bed frame that acts as the hinge point for flexing or breaking of the bed into the 30 degree position.

In one example of installation on bed, the bed is first inspected for the joint or pivot point. The overlay device or apparatus is then placed on the bed so that the central point or 0.5 inch circular weld within the central 4×4 inch relief chamber at the epicenter 328 of the overlay is directly over this joint or hinge point in the bed. Lastly, the overlay is attached to the bed frame at all four corners of the overlay using the one or more straps 326. In one embodiment, the straps 326 may be 1 inch Velcro straps; however any straps that can hold overlay to the bed can be used. The overlay can be placed directly on the mattress and covered by a fitted sheet or it can be attached to the bed over the fitted sheet. A protective sleeve can be places over the overlay to protect it and reduce cleaning requirements.

Once a patient is placed on the bed over the overlay device or apparatus, the patient is in a location known to or actively oriented by the device or apparatus and the control system can then inflate (pressurize) and deflate (depressurize) the pressure relief chambers of the relieving portion of the overlay in a preprogrammed cycle for specific time/pressure values to optimize the pressure-relieving capabilities of the system. The pressure and timing cycles are also unique and specific to the design of the system. The pressure and timing cycles may take into account the weight of the patient, the position of the bed, and/or the type of surface on which the overlay is resting, etc. The pressures used by the control system may be calculated to be the minimal pressures needed to achieve even redistribution of high pressure. Interface pressure may be determined by the patient's weight and body position. The greater the weight, the greater the downward pressure of the patient on the overlay, and thus the greater the internal pressure will need to be in order to lift the patient off the underlying mattress in order to affect the redistribution of pressure from high points to low points. This data may be programmed into the controller by the healthcare team prior to use and is specific for each patient.

In one embodiment, the surface area of the pressure-mitigating contact portion 322 (e.g., or pressure relief surface) of the pressure mitigation support apparatus 320 is designed to match the size of the patient's anatomy in the region of contact made between the patient's sacral region and the apparatus. Thus, the size of the pressure-mitigating contact portion 322 is the size of the patient's surface anatomy between the patient's lower back to the mid-thigh region (i.e., the sacral region). The sacral region is typically a 20×20 square inch area for the standard adult male of 75 Kg. In some embodiments, the pressure mitigation support apparatus 320 may be size matched to the patient. For example, the pressure mitigation support apparatus 320 may come in various sizes such as small, medium, large, extra-large, etc. The sizes may thus range from a 12×12 square inch area to a 35×35 (or greater) square inch area.

The pressure-mitigating contact portion 322 is also patient size specific and designed to mirror the size of the patient. Thus, the device or apparatus can have several sizes depending on the patient's anatomy (e.g., small, medium, large, extra-large, etc.). The device or apparatus is designed so that when sized appropriately, the side supports 325 will gently contact the hips of the patient on each side therefore aligning the patient over the device such that the patient's anatomy is aligned with the apparatus design which was patterned on the human anatomy.

In one embodiment, ideal patterns include designs that when any given pressure relief chamber is deflated, the pressure relief chambers that remain inflated are still effective in comfortably supporting the weight of the patient such that a low pressure area is created and maintained in the area of the deflated relief chamber region by effectively holding up the patient in the regions where the relief chambers remain inflated. This means that the relief chambers must be neither too large nor too small in any given area or region. In one embodiment, each of the three relief chambers represent around 33% of the total surface area device within a 20×20 square inch area of the sacral region.

With typical support surfaces (e.g., standard hospital bed) a standard mattress or support surface is 36 inches wide. Accordingly, patients using these devices still have ample room between the patient and a side support (or bolster) which allows them to move side to side (laterally). As a result with typical or current support surfaces a patient is not held in a specific location, and thus the typical support surface cannot be anatomy specific.

For a device that is specifically designed to function optimally when located beneath the patient's anatomy in a specific location, then the ability to move around freely over the surface would render that support surface ineffective as the patient and the anatomy specific pattern would not be controlled by the addition of the side bolsters. This differs from other full mattress overlays or mattress support surfaces that are not sized to matched in size to the contact surface of the patient's anatomy but are much larger—i.e. standard bed size of 72 inches×36 inches. Most adult patients (ave 75 kg) unless extremely obese are on average 20 inches wide.

In one embodiment, the pressure relief surface is also contoured to fit the patient's surface topography in the sacral region (i.e., larger in height to the lateral aspects of the relief surface and shorter in height to the center of the pressure relief surface). This contour creates a bowl shape from side to side in the region of the pressure relief surface that compliments the human topography of the sacral region. This is in distinction to the consideration of the internal anatomy, namely blood vessels, muscle and bony anatomy. This internal anatomy is considered in the pattern (not height) of the air cell design which is distinct from considerations of surface topography that dictate the vertical height of the inflated air cells to accommodate variation in the surface contours of the human anatomy. Inflation of the apparatus can result in a bowl shape.

The bowl shape is designed to create an even distribution of pressure when all the air cells of the pressure relief surface are inflated. The result of the bowl shape is to maximally redistribute pressure away from the central area where pressure injury is most common—namely at the top of the gluteal fold. The pressure is displaced to a more lateral location towards the hips. The 3-D nature or differences in vertical height throughout the inflated pressure relief surface is not utilized in prior art designs. Further, the diameter or vertical height of the inflated pressure relief chambers that make up the pressure relief surface are specifically designed to be of a suitable height so as not to be so large as to create mal-alignment of the long axis (spine) of the patient but also not of a height that would be to small as to be ineffective as a pressure relief surface. This vertical height is roughly 2-3 inches on average.

FIG. 4A and FIG. 4B depict top and cross-sectional views, respectively, of an example pressure mitigation support apparatus 400, according to an embodiment. The pressure mitigation support apparatus 400 includes side supports 425 and a pressure-mitigating contact portion 422. The pressure-mitigating contact portion 422 includes a plurality of independently pressurized relief chambers 427. The independently pressurized relief chambers 427 are configured in a specific geometric pattern that effectively mitigates contact pressure between a support surface and a specific anatomic region of the patient's body when the specific anatomic region of the patient's body is oriented over an epicenter of the geometric pattern. The pressure mitigation support apparatus 400 may be, for example, the pressure mitigation support apparatus 120 of FIG. 1; although alternative configurations are possible.

As discussed above, the pressure mitigation support apparatus 400 includes channel tubing 436. The channel tubing 436 is separate from the pressure relief surface portion of the device but can be incorporated into the design of the device such that the tubing will follow the seams or channels between the pressure relief surfaces where adjacent independently pressurized relief chambers meet. In one embodiment, the channel(s) are recessed into the seams when the relief chambers 427 are pressurized and/or otherwise inflated. Thus, once the relief chambers 427 are pressurized and/or otherwise inflated, the channel tubing 436 does not make physical contact with the patient. Additionally, the channel tubing 436 does not contribute to the pressure mitigation function of the device or apparatus. That is, the channel tubing 436 serves only to circulate pressure (e.g., air, liquid, etc.) between the seams or recessed channels created by the relief chambers 427.

In one embodiment, the pressure that exits the channels does not originate from the relief chambers of the pressure relief surfaces. For example, the pressure that exits from the multi-channel tubing can originate from its own separate source. The pressure or flow from the pressure channels is controlled by a control system such as, for example, the control system 130 of FIG. 1. The control system can control the pressure (e.g., the air supply) and not by the internal pressure of an air-filled bladder that comprises a portion of a pressure relieving surface as is the case when a device is configured as a low air loss surface.

The channel tubing 436 is designed as a passive conduit and not as chamber designed to inflate. The channel tubing 436 may be designed not for low air loss as is the case with previously described low air loss surfaces that leak a low amount of air from the internal reservoir of the inflated support surface, but the air channels described here deliver do not leak a high volume of air or gas dedicated only to this purpose and none other. The rate of air flow from the channels is precisely controlled by a flow meter and not dependent on internal pressures created within the device as is the case with the low air low surfaces. The channels may have one or more openings for the release of air. The control of the volume of air delivered and not "lost" from the surface is under strict control for the device as is not the case of low air loss surfaces. (Volume not pressure control). In a low air loss setting, if the openings are blocked by the weight of the patient, the air which is at the set pressure of the pressure relieving air chamber will stop flowing. This is different for the air channels described here where the air is delivered by volume control. If the openings to deliver the air are blocked by the weight of the patient, the pressure of the delivered air will continue to rise until it is greater than the external force blocking the openings of the air channels. This variable pressure is not possible in a low air loss configuration. Volume control delivery in a low air loss setting would also control the pressure within the air chamber of the support surface which is undesirable.

Figure 5:
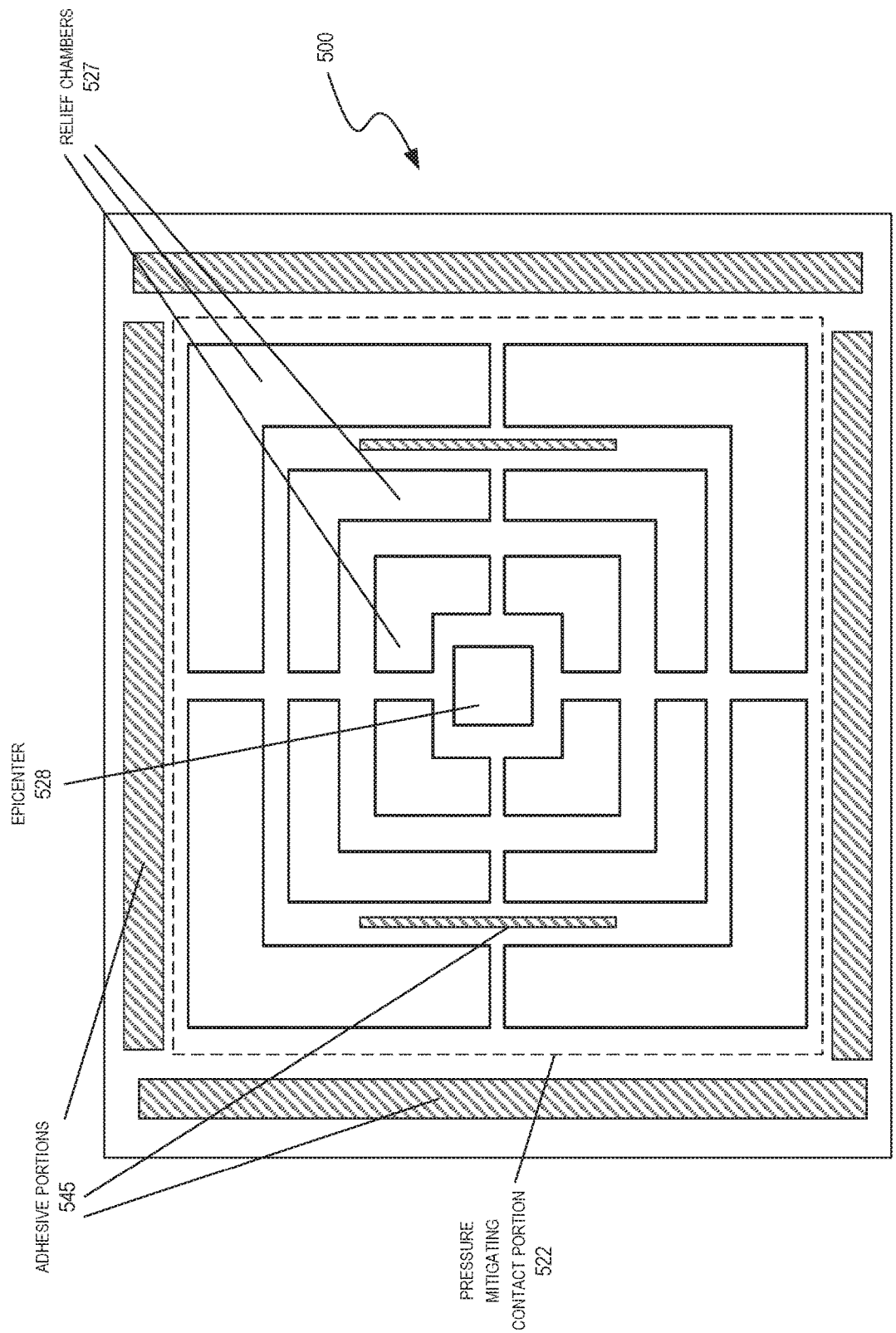
FIG. 5 depicts an example pressure mitigation support apparatus, according to an embodiment.

FIG. 5 depicts an example pressure mitigation support apparatus 500, according to an embodiment. The pressure mitigation support apparatus 500 includes a pressure-mitigating contact portion 222 and one or more adhesive portions 545. The pressure-mitigating contact portion 222 includes a plurality of independently pressurized relief chambers 527. In this example, the independently pressurized relief chambers 527 are configured in a specific geometric "C-shape" pattern that mitigates contact pressure between a support surface and a specific anatomic region of the patient's body when the specific anatomic region of the patient's body is oriented over an epicenter of the geometric pattern. The one or more adhesive portions are interconnected on the mitigation support apparatus 500. The adhesive portion may be configured to actively orient the specific anatomic region of the patient's body over the epicenter 528 of the geometric pattern through one or more biocompatible adhesives. Although the pressure mitigation support apparatus 500 is shown without side supports, it is appreciated that such supports may be included in some embodiments.

In the example, of FIG. 5, the one or more adhesive portions 545 are shown with cross shading. The one or more adhesive portions 545 may be biocompatible adhesive portions that extend along a section of the perimeter of the contact pressure-mitigation support apparatus. Alternatively or additionally, the one or more adhesive portions 545 may extend along at least a section of one or more of the plurality of the independently pressurized relief chambers such as, for example, the "C-shaped" independently pressurized relief chambers.

In one embodiment, the one or more adhesive portions 545 can be adhered directly to the area of concern via a biocompatible adhesive such as, for example, the adhesive material used in common medical band-aids. In this case, the pressure mitigation support apparatus 500 may essentially act as an inflatable band-aid "like" device that could be in the form of the two "C-shapes" around a central area of ulceration or a central area at risk of ulceration.

FIG. 6 depicts a flow chart illustrating an example process 600 for coordinated chamber inflation and deflation of a therapeutic surface to stimulate blood flow and reduce pressure while a spatial relationship between a patient and a therapeutic surface is controlled by side-walls of the therapeutic surface.

As discussed, the inflatable support surface is comprised of the two side walls and a center portion with multiple separate air bladders (or chambers) designed in a specific pattern to best preserve blood flow and reduce pressure when inflated and deflated in a coordinate fashion that is controlled by settings in the air pump control device. Process 600 describes the coordinated chamber inflation and deflation of a therapeutic surface according to one embodiment.

In step 610, an air pump control system such as, for example, air pump control system 130 of FIG. 1 determines an initial pressure for each of a plurality of independently pressurized chambers built into a therapeutic support surface. In step 612, the air pump control system initializes one of more of the settings. The initialization of the setting can include selecting a program and/or one or more pressure timers. The pressure timers can control when and if to change the pressure at an individual chamber. In one embodiment, each chamber has its own timer. However, in other embodiments, some chambers may share timers. Further, any of the chamber timers can be configured to work in concert. In one embodiment, one or more of the initialization settings can be based on the patient (e.g., weight, age, pre-programmed, etc.). In step 614, the air pump control system checks to see if a timer has expired, and if so, in step 616, the air pump control system adjusts the pressure in the associated chamber accordingly.

Figure 7:
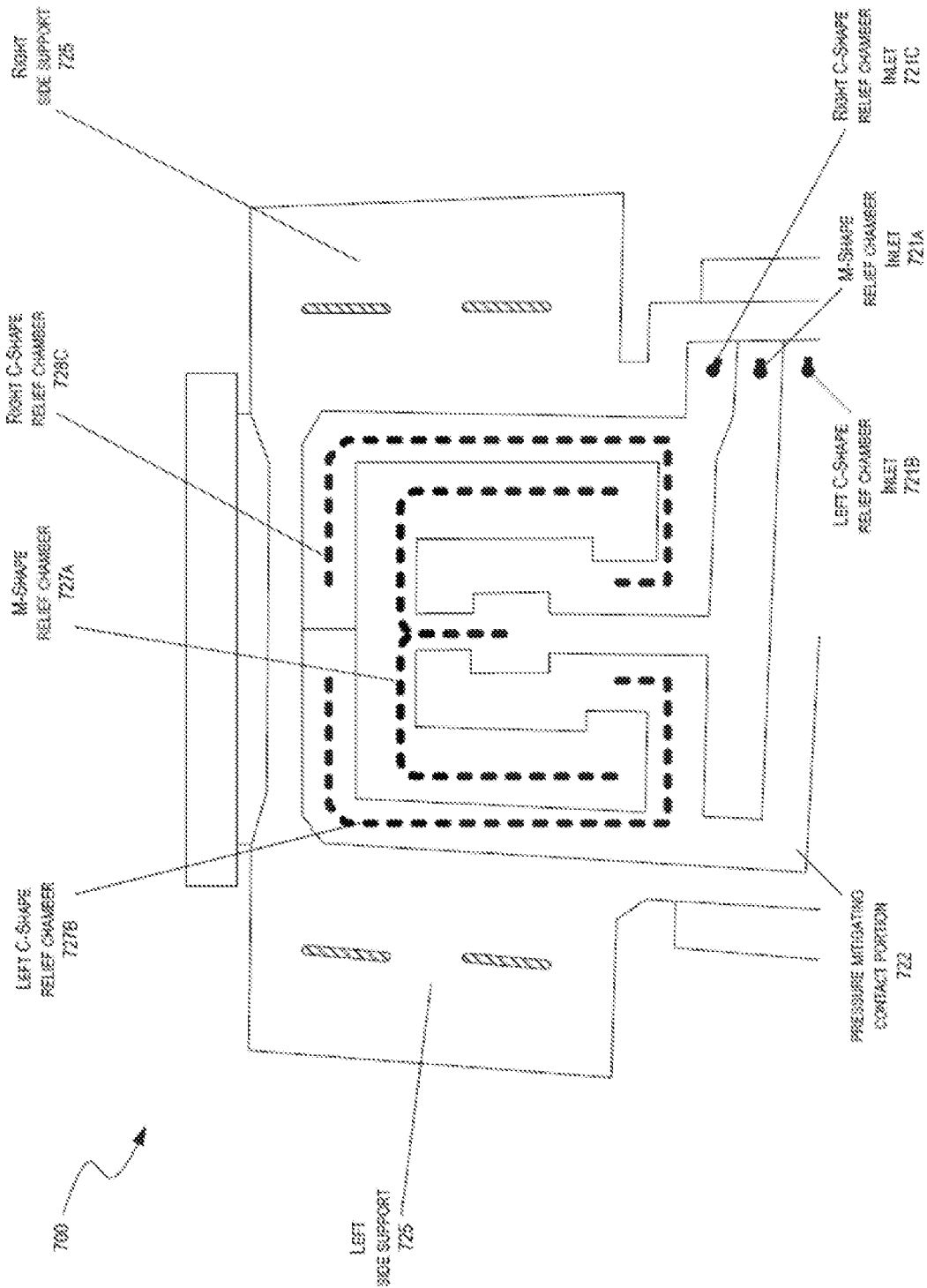
FIG. 7 depicts a schematic diagram illustrating an example pressure mitigation support apparatus, according to an embodiment.

FIG. 7 depicts a schematic diagram illustrating an example pressure mitigation support apparatus 700, according to an embodiment. The pressure mitigation support apparatus 700 includes side supports 725 and a pressure-mitigating contact portion 422. The pressure-mitigating contact portion 722 includes a plurality of independently pressurized relief chambers 727. The pressure mitigation support apparatus 700 may be, for example, the pressure mitigation support apparatus 120 of FIG. 1; although alternative configurations are possible.

In one embodiment, the independently pressurized relief chambers 727 are configured in a specific geometric pattern that effectively mitigates contact pressure between a support surface and a specific anatomic region of the patient's body when the specific anatomic region of the patient's body is oriented over an epicenter of the geometric pattern. For example, in the example of FIG. 7, three independently pressurized relief chambers 727 are shown: M-shaped relief chamber 727a, left c-shaped relief chamber 727b, and right c-shaped relief chamber 728c. These relief chamber receive pressure or air from corresponding inlets 721.

In one embodiment, the geometric pattern includes the first independently pressurized relief chamber 727a which intersects the epicenter of the geographic pattern, and second and third independently pressurized relief chambers, 727b and 727c, respectively, that collectively encompass the first independently pressurized relief chamber. More specifically, in the example of FIG. 7, the first independently pressurized relief chamber 727a generally comprises an M-shape with the epicenter of the geometric pattern residing at the internal angle formed by the intersecting planes of the M-shape, and the second independently pressurized relief chamber 727b generally comprises a C-shape that encompasses a left-most bisection of the first independently pressurized relief chamber, and the third chamber 727c comprises a symmetric mirror image of the second chamber about the bisection of the first chamber.

Figure 8:
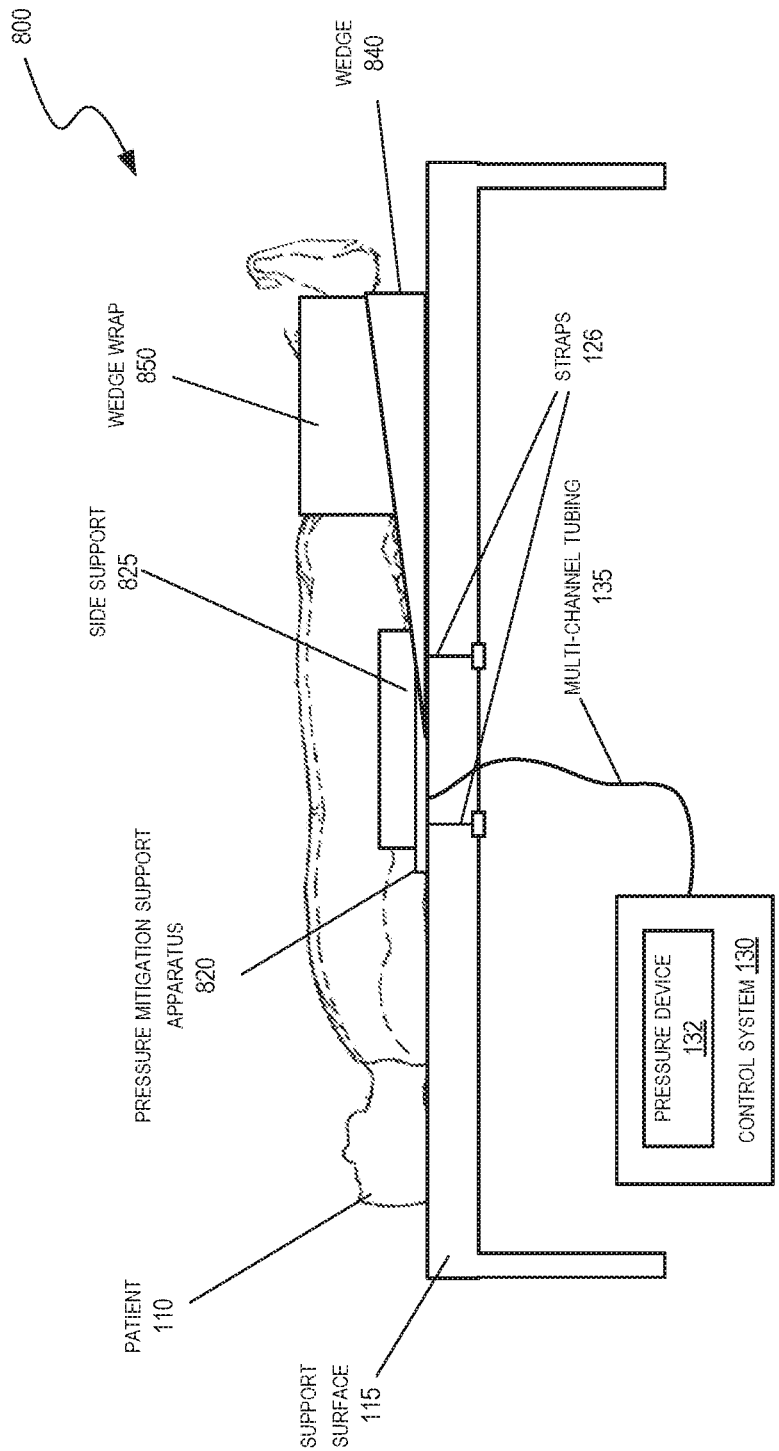
FIG. 8 depicts a side view of an example system for orienting a patient over an anatomy-specific pressure-mitigating contact surface with lower extremity wedge on which the patient rests, according to an embodiment.

FIG. 8 depicts a side view of an example system 800 for orienting a patient over an anatomy-specific pressure-mitigating contact surface with lower extremity wedge on which the patient rests, according to an embodiment. The example of FIG. 8 is similar to the example of FIG. 1, however the pressure mitigation support apparatus 820 includes a lower extremity wedge 840 and an optional wedge wrap 850.

In one embodiment, the lower extremity wedge 840 is an inflatable wedge that is designed to fit (or sit) beneath the lower extremities of the user. The lower extremity wedge 840 can elevate the legs to provide additional benefits to a patient or user. In one embodiment, the lower extremity wedge 840 can be attached to or be part of (integrated into or with) the side supports 825.

In one embodiment, the lower extremity wedge 840 can prevent the migration of the user toward the foot of the bed (lengthwise movement) and/or can act to further maintain the position of the user over the pressure mitigation support (PMS) apparatus 820 in the Y-axis.

As discussed above, in one embodiment, the pressure mitigation support apparatus can comprise an overlay that can be extended behind a patient's lower extremities to include a wedge 840 configured to elevate the legs in order to prevent the user from moving toward the foot of the bed. Accordingly, the wedge 840 aids in the control of the user's location over the pressure mitigation support apparatus. As the side air bolsters (side supports 825) orient the user's location over the pressure mitigation support apparatus 820 so too does the wedge 840 behind the lower extremities by preventing the user from moving toward the foot of the bed when the head of the bed is elevated. In one embodiment, the wedge 840 lifts the lower extremities when in use and protects the user's heals.

In one embodiment, the pressure mitigation support apparatus 820 (or the wedge 840) includes a wedge wrap 850. The wedge wrap 850 can be configured to wrap around the lower extremities to serve both as a deep venous thrombosis prevention device and a pressure ulcer prevention device. Accordingly, in operation, the wedge 840 can lift the lower extremities (e.g., a user's or patient's heels) from the support surface 115 leaving the heels less prone to the formation of pressure ulcers.

In one embodiment, all or part of the wedge 840 can be removably detachable from the pressure relieving portion (i.e., the pressure migration support apparatus 820) or it may be constructed as one unit.

Figure 9:
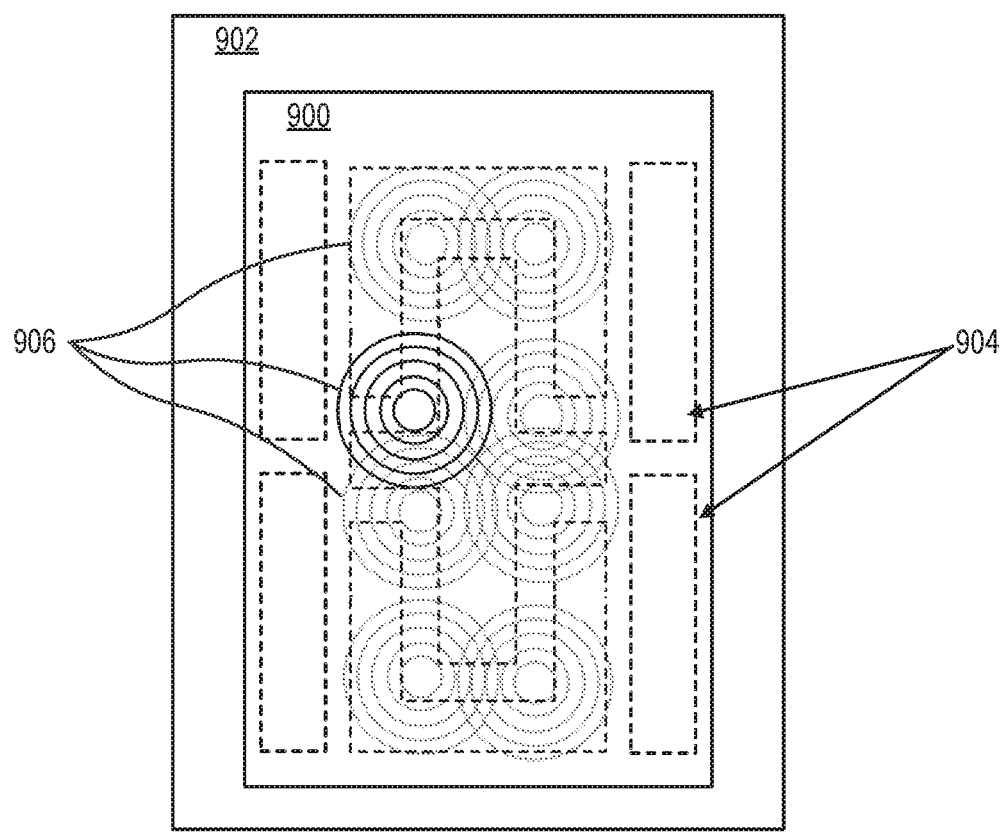
FIG. 9 is a partially schematic top view of a pressure-mitigation apparatus illustrating varied pressure distributions for avoiding ischemia for a mobility impaired patient in accordance with embodiments of the present technology.

FIG. 9 is a partially schematic top view of a pressure-mitigation apparatus 900 (also referred to as a "pressure-mitigation device" or a "pressure-mitigation pad") illustrating varied pressure distributions for avoiding localized ischemia and resulting reperfusion injury for a mobility impaired patient (e.g., immobilized and/or bed-ridden patients) in accordance with embodiments of the present technology. As discussed above, when a human body is supported by a contact surface 902 for an extended duration, pressure injuries may form over bony prominences such as the skin overlying the sacrum, coccyx, heels, or hips. These bony prominences often represent the location or locations at which the most pressure is applied by the contact surface 902 and, therefore, may be referred as the "main pressure point(s)" along the surface of the human body. To prevent the formation of pressure injuries, healthy individuals periodically make minor positional adjustments (also known as "micro-adjustments") to shift the location of the main pressure point. However, individuals having impaired mobility often cannot make these micro-adjustments by themselves. Mobility impairment may be due to physical injury (e.g., a traumatic injury or a progressive injury), movement limitations (e.g., within a vehicle, on an aircraft, or in restraints), medical procedures (e.g., those requiring anesthesia), and/or other conditions that limit an individual's natural movement. For these mobility impaired individuals, the pressure-mitigation apparatus 900 can be used to shift the location of the main pressure point(s) on their behalf. That is, the pressure mitigation apparatus 900 creates moving pressure gradients to avoid sustained, localized vascular compression and enhance tissue perfusion.

As shown in FIG. 9, the pressure-mitigation apparatus 900 can include a series of chambers 904 (also referred to as "cells") whose pressure can be individually varied. The chambers 904 may be formed by interconnections between a first or top layer and a second or bottom layer of the pressure-mitigation apparatus 900. The top layer may be comprised of a first material (e.g., an air-permeable, non-irritating material) configured for direct contact with a human body, while the bottom layer may be configured of a second material (e.g., a non-air-permeable, gripping material) configured for direct contact with the contact surface 902 on which the pressure-mitigation apparatus 900 is placed. In these and other embodiments, the top layer and/or the bottom layer can be comprised of more than one material, such as a coated fabric or a stack of interconnected materials.

A pump, such as the pressure device 132 described above with respect to FIG. 8, can be connected to each chamber 904 (e.g., via a corresponding inlet valve), and controllably vary the pressure in each chamber 904 on an individual basis in accordance with a predetermined pattern. As further described below, the pump and associated controller can operate the series of chambers 904 in several different ways. In some embodiments, the chambers 904 have a naturally deflated state, and the pump can be programmed to inflate at least one of the chambers 904 to shift the main pressure point along the anatomy of the user. For example, the pump may be programmed to inflate at least one of the chambers 904 located directly beneath an anatomical region to momentarily apply contact pressure to that anatomical region and relieve the contact pressure on the surrounding anatomical regions adjacent to the deflated chambers 904. In these and other implementations, the pump may be programmed to inflate two or more chambers 904 adjacent to an anatomical region to create an open space or void beneath the anatomical region to shift the main pressure point at least momentarily away from the anatomical region. In other embodiments, the chambers 904 have a naturally inflated state, and the pump can be programmed to deflate at least one of the chambers 904 to shift the main pressure point along the anatomy of the user. For example, the pump may be configured to deflate at least one of the chambers 904 located directly beneath an anatomical region, thereby forming a void beneath the anatomical region to momentarily relieve the contact pressure on the anatomical region. Whether configured in a naturally deflated or naturally inflated state, the continuous or intermittent alteration of the inflation levels of the individual chambers 904 moves the location of the main pressure point across different portions of the human body. As shown in FIG. 9, for example, inflating and/or deflating the chambers 904 creates temporary contact regions 906 that move across the pressure-mitigation apparatus 900 in a predetermined pattern, and thereby changing the location of the main pressure point(s) on the human body for finite intervals of time. Thus, the pressure-mitigation apparatus 900 can simulate the microadjustments made by mobile individuals to relieve stagnant pressure application caused by the contact surface 902.

As noted above, the series of chambers 904 may be arranged in an anatomy-specific pattern so that when the pressure within one or more individual chambers is altered, the contact pressure on a specific anatomical region of the patient is relieved (e.g., by shifting the main pressure point elsewhere). As shown in FIG. 9, for example, the main pressure point can be moved between eight different locations corresponding to the eight temporary contact regions 906. In some embodiments the main pressure point shifts between these locations in a predictable manner (e.g., in a clockwise or counter-clockwise pattern), while in other embodiments the main pressure point shifts between these locations in an unpredictable manner (e.g., in accordance with a random pattern, a semi-random pattern, and/or detected pressure levels). Those skilled in the art will recognize that the quantity and position of these temporary contact regions 906 may vary based on the arrangement of the series of chambers 904, the anatomical region supported by the pressure-mitigation apparatus 900, the characteristics of the human body supported by the pressure mitigation apparatus 900, and/or the condition of the user (e.g., completely immobilized, partially immobilized, etc.).

In some embodiments, the pressure-mitigation apparatus 900 does not include side supports because the patient's condition may not benefit from the positioning provided by the side supports. For example, side supports can be omitted when the patient is medically immobilized (e.g., under anesthesia, in a medically induced coma, etc.) and/or physically restrained by the underlying support surface (e.g., rails along the side of a bed, arm rests on the side of a chair) and/or other structures (e.g., physically restraints holding down the patient, casts, etc.).

Figure 10A:
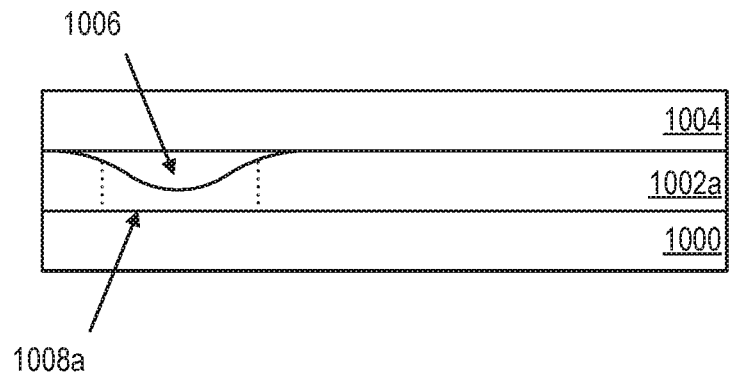
FIG. 10A is a partially schematic side view of a pressure-mitigation apparatus for relieving pressure on a specific anatomical region by deflating at least one chamber in accordance with embodiments of the present technology.

FIG. 10A is a partially schematic side view of a pressure-mitigation apparatus 1002*a* for relieving pressure on a specific anatomical region by chamber deflation in accordance with embodiments of the present technology. The pressure-mitigation apparatus 1002*a* is positioned between a contact surface 1000 (e.g., a bed, table, or chair) and a human body 1004 and, to relieve pressure on a specific anatomical region of the human body 1004, at least one chamber 1008*a* of a plurality of chambers (referred to collectively as "chambers 1008") proximate to the specific anatomical region at least partially deflates to create an open space or void 1006*a* beneath the specific anatomical region. In such embodiments, the remaining chambers 1008 may remain inflated. Thus, the pressure-mitigation apparatus 1002*a* may sequentially deflate chambers 1008 (or arrangements of multiple chambers) to relieve the contact pressure applied to the human body 1004 by the contact surface 1000.

Figure 10B:
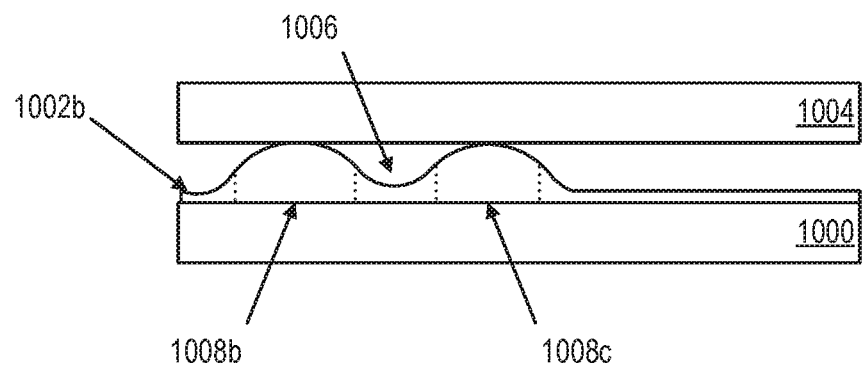
FIG. 10B is a partially schematic side view of a pressure-mitigation apparatus for relieving pressure on a specific anatomical region by inflating at least one chamber in accordance with embodiments of the present technology.

FIG. 10B is a partially schematic side view of a pressure-mitigation apparatus 1002*b* for relieving pressure on a specific anatomical by chamber inflation in accordance with embodiments of the present technology. For example, to relieve pressure at a specific anatomical region of the human body 1004, the pressure-mitigation apparatus 1002*b* can inflate two chambers 1008*b* and 1008*c* disposed directly adjacent to the specific anatomical region to create a void 1006*b* beneath the specific anatomical region. In such embodiments, the remaining chambers may remain at least partially deflated. Thus, the pressure-mitigation apparatus 1002*b* may sequentially inflate a chamber (or arrangements of multiple chambers) to relieve the contact pressure applied to the human body 1004 by the contact surface 1000.

In some embodiments, the pressure-mitigation apparatuses 1002*a* and 1002*b* of FIGS. 10A and 10B can have the same configuration of chambers 1008, and can operate in both a normally inflated state (described with respect to FIG. 10A) a normally deflated state (described with respect to FIG. 10B) based on the selection of the operator (e.g., a medical professional or the user). For example, the operator can use a controller to select a normally deflated mode such that the pressure-mitigation device operates as described with respect to FIG. 10A, and then change the mode of operation to a normally inflated mode such that the pressure-mitigation device operates as described with respect to FIG. 10B. Thus, the pressure-mitigation apparatuses disclosed herein can shift the location of the main pressure point by controllably inflating the chambers, controllably deflating the chambers, or a combination thereof.

FIG. 11 is a flow diagram of a process 1100 for treating a condition using a pressure-mitigation apparatus in accordance with embodiments of the present technology. In step 1102, a medical professional diagnoses a high-risk, perfusion-challenged, mobility-impaired patient, whose state can be improved by increased blood flow and a decreased presence of proinflammatory mediators. For example, such patients may include those subject to a condition that causes prolonged sedentary or immobile periods. Examples of conditions that may be improved by increased blood flow and a decreased presence of proinflammatory mediators include burns, trauma, pressure injury, ischemia, strokes, Parkinson's disease, and/or various other diseases or injuries. These conditions are improved, at least in part, by reducing the likelihood of or preventing ischemia and reperfusion injury and, thereby, inhibiting or preventing the release of proinflammatory mediators.

In step 1104, the medical professional determines an appropriate treatment regimen for the condition. For example, if the condition is a pressure ulcer, the medical professional may determine the appropriate conventional treatment regimen should include reducing pressure on the corresponding anatomical region (e.g., by repositioning the patient), cleaning/dressing the wound, and/or excisional debridement of necrotic and/or infected tissue. As another example, if the condition is a stroke, the medical professional may determine the appropriate treatment regimen should include therapy with clot-busting drugs (e.g., a tissue plasminogen activator), treatment with endovascular procedures (e.g., insertion of a catheter or a stent), and/or other conventional stroke-related treatments. As another example, if the condition is ischemia, the medical professional may determine the appropriate conventional treatment regimen should include administration of a medication (e.g., aspirin, nitrates, beta blockers, calcium channel blockers, cholesterol-lowering medications, angiotensin-converting enzyme (ACE) inhibitors, or ranolazine), angioplasty/stenting, coronary artery bypass surgery, enhanced external counterpulsation, and/or other conventional ischemia-related therapies.

To enhance or expedite the treatment of the diagnosed conditions, the medical professional or someone else associated with the treatment protocol may choose to augment the normal treatment regimen by incorporating the use of a pressure-mitigation apparatus (e.g., the pressure-mitigation apparatuses described with respect to FIGS. 10A-10B above). The pressure-mitigation apparatus can be placed between the patient and a contact surface, such as a patient bed, a surgical table, and/or other surface used to support the patient, and activated to shift the main pressure point of the contact pressure across different regions on the surface of the patient's body, thereby enhancing blood flow between the patient's body and the contact surface (step 1106). To shift the main pressure point of the contact pressure, a series of chambers of the pressure-mitigation apparatus can be controllably inflated, deflated, or any combination thereof (e.g., as described with respect to the pressure-mitigation apparatuses of FIGS. 10A-10B). The series of chambers can be generally arranged in an anatomy-specific pattern. Consequently, the series of chambers may be inflated/deflated in such a manner to improve blood flow around the anatomical region for which the pressure-mitigation apparatus is designed. Thus, the pressure-mitigation apparatus may include different arrangements of chambers depending on whether it is designed to improve blood flow to the sacral region, lumbar region, thoracic region, and/or other anatomical region of the body. While embodiments may be described in the context of improving blood flow to the dorsal side of a human body, those skilled in the art will recognize that pressure-mitigation apparatuses may be designed to improve blood flow to other sites (e.g., the ventral side of the body, the elbows, knees, ankles, shoulders, or cranium) as well.

In step 1108, treatment of the condition can continue in accordance with the treatment regimen prescribed for the condition. However, several benefits are expected result due to the increased blood flow resulting from deployment of the pressure-mitigation apparatus and associated system. In some instances, the overall treatment of the patient may require less equipment than would otherwise be necessary. For instance, deployment of the pressure-mitigation apparatus may allow for the use of standard hospital beds, and lessen or eliminate the need for certain expensive, space-consuming equipment therapy beds, therapeutic/pressure relief cushions, pressure redistribution overlays, and/or heel offloading devices. The use of the pressure-mitigation system can also reduce the amount of manual care (e.g., from nurses, doctors, etc.) than would otherwise be necessary to manually shift the location of the main pressure point along the dorsal side of a patient (e.g., by turning the patient) during periodic time intervals. In addition, it is expected that the incorporation of pressure-mitigation systems can reduce the overall use of medication because the system may reduce or prevent the generation of inflammatory mediators, which increase pain, inflammation, and exacerbate certain conditions. Accordingly, less medication (e.g., pain relievers) may be needed to treat the secondary conditions that typically occur from long periods of immobilization. Furthermore, the incorporation of pressure-mitigation systems inhibits or prevents ischemia and reperfusion injury and, therefore, is expected to lead to shorter overall hospital stays (also referred to as "length of stay" or "LOS"). More specifically, by inhibiting or preventing ischemia and reperfusion injury, the pressure-mitigation system reduces the production of excess proinflammatory mediators that can eventually circulate through the blood stream. With less proinflammatory mediators, the pressure-mitigation system reduces systemic inflammation and prevents these mediators from circulating to other areas of the body (e.g., the brain) where they can cause localized inflammation, increase damage, and/or worsen other conditions. Moreover, pressure-mitigation apparatuses can be readily deployed in non-hospital settings (e.g., in a patient's home) to allow treatment to continue in non-hospital settings.

Selected Clinical Examples Exhibiting Impact of Improved Blood Flow

Several different studies have been performed to illustrate the effects of deploying pressure-mitigation apparatuses, such as the pressure mitigation apparatuses and systems described above, to enhance perfusion for treatment of sacral region injuries (e.g., pressure ulcers) and other ischial pressure injuries. These studies will be discussed in greater depth below.

A clinical study was performed to compare the time it took to fully heal patients with stage 2 pressure injuries managed with pressure-mitigation apparatuses with the time it took to fully heal a size-matched cohort of patients with stage 2 pressure injuries managed with conventional alternating-pressure mattresses. The study enrolled 31 patients that resided in 4 community-based, long-term care facilities.

Patients in the control group were provided with a low-air-loss mattress capable of alternating pressure in accordance with the corresponding facility's treatment protocol for stage 2 pressure injuries. Patients in the experimental group were provided with the pressure-mitigation apparatuses described herein rather than a low-air-loss mattress. For each patient in the experimental group, the pressure-mitigation apparatus was installed on top of a standard static-foam mattress or a standard recovery chair. Both groups otherwise received an identical standard of care.

The primary outcome measure was the time for complete healing of the stage 2 pressure injuries. Kaplan-Meir and log-rank tests were calculated to analyze the time-to-heal data, and then generate the comparison results. Patient characteristics were compared using standard t-tests for data sets and Chi-squared tests for proportions to ensure that the differences in average values and ratios between the control and experimental groups were not statically significant.

As shown in Table I, 9 patients in the experimental group with 14 stage 2 pressure injuries completed the trial, and 22 patients in the control group with 28 stage 2 pressure injuries were identified for comparison purposes. Various characteristics of these patients are provided in Table II.

TABLE I

Summary of trial participants.

|  | Control Group | Experimental Group | Total |
|---|---|---|---|
| Patients Enrolled | 22 | 10 | 32 |
| Patients Withdrawn | 0 | 1 | 1 |
| Patients Completing Trial | 22 | 9 | 31 |
| Number of Pressure Injuries | 28 | 14 | 42 |

TABLE II

Characteristics of trial participants.

|  | Control Group | Experimental Group | P-Value | Statistically Significant Difference? |
|---|---|---|---|---|
| Mean Age (Years) | 82 | 84.86 | 0.46 | No |
| Mean Pressure Injury Size (cm$^2$) | 1.8 | 1.5 | 0.64 | No |
| Mean Braden Scale | 16.04 | 15.50 | 0.61 | No |
| Male Patient Percent | 45.5% | 11.11% | 0.07 | No |
| Wheelchair Use Percent | 86.36% | 100% | 0.25 | No |
| Incontinent Percent | 77.27 | 66.67 | 0.55 | No |

The mean time to fully heal the pressure injuries for the control group was 26.25 days with a standard deviation of 2.42 days and upper/lower 95% confidence boundaries of 21.51 days and 30.99 days, respectively. In contrast, the mean time to fully heal the pressure injuries for the experimental group was 10.50 days with a standard deviation of 1.02 days and upper/lower 95% confidence boundaries of 8.51 days and 12.49 days, respectively. Thus, the mean time to fully heal for the experimental group was roughly 40% of the mean time to fully heal for the control group. Over the course of the study, patients in the control group took roughly 150% longer to fully heal from their stage 2 pressure injuries than those patients who were treated with the pressure-mitigation apparatuses described herein. Accordingly, the pressure-mitigation systems disclosed herein have been shown to significantly decrease the overall healing time of pressure injuries in comparison to low-air-loss alternating pressure mattresses.

In a patient study, a pressure-mitigation system as disclosed herein was shown to expedite the healing of a stage 3 pressure injury. An 81-year-old male patient sustained three ischemic strokes, was eventually discharged on hospice care, and, within a week of being home, the patient developed a stage 3 pressure injury despite being turned by medical staff every two hours and also caused additional distress and pain. The wound was initially treated with collagenase-based ointment and intermittent use of foam dressings. Additional nursing staff was also hired to provide more frequent turning.

The treatment regime was modified to supplement the incremental turning of the patient with a pressure-mitigation apparatus affixed to the patient's bed. The pressure-mitigation apparatus was from thereon used continuously, and complete healing of the stage 3 pressure injury occurred 52 days following deployment of the pressure-mitigation apparatus. Additional information on the healing trajectory of the stage 3 pressure injury are provided in Table III. In addition, after introduction of the pressure-mitigation apparatus, the patient indicated a higher level of comfort and requested a substantial reduction in the frequency of repositioning. Indeed, the speed at healing after introduction of the pressure-mitigation apparatus allowed for a significant decrease in the turn frequency. It is expected that the introduction of the pressure-mitigation apparatus to the patient's treatment regime significantly reduced overall healing time in comparison to the only using intermittent turning protocols.

TABLE III

Healing trajectory of a stage 3 pressure injury.

|  | Length (cm) | Width (cm) | Depth (cm) | Volume (cm$^3$) | Percentage Healed from Previous Week | Percentage Healed from Initiation of Pressure-Mitigation Apparatus |
|---|---|---|---|---|---|---|
| October 17 | 1.0 | 1.0 | 0.0 | N/A | N/A | N/A |
| October 24 | 3.2 | 2.0 | 0.1 | 0.64 | N/A | N/A |
| October 30 | 3.5 | 2.0 | 0.1 | 0.70 | −109% | N/A |
| November 6 | 2.5 | 2.0 | 0.1 | 0.50 | 29% | 29% |
| November 16 | 1.5 | 1.5 | 0.1 | 0.23 | 54% | 68% |
| November 27 | 0.5 | 0.5 | 0.0 | N/A | 100% | 96% |
| December 7 | 0.0 | 0.0 | 0.0 | N/A | 100% | 100% |

In another patient study, a pressure-mitigation system as disclosed herein was shown to reduce the duration of healing of a stage 4 sacral pressure injury. A 64-year-old male patient sustained a level 4 cervical spine fracture with incomplete spinal cord injury, paraplegia, and impaired sensation. After the acute and rehabilitative treatment had been administered, the patient was admitted to a nursing facility for long-term care. Thereafter, the patient was diagnosed with a stage 4 pressure injury, and then treated with sharp surgical debridement and negative pressure wound therapy (NPWT).

After 132 days, a pressure-mitigation apparatus was introduced to the treatment regimen. Complete healing of the stage 4 pressure injury occurred in 118 days following deployment of the pressure-mitigation apparatus. Additional conversations with the patient suggested that the pressure-mitigation apparatus was also effective in reducing the pain associated with pressure injuries and mobility impairment. Additional information on the healing trajectory of the stage 4 pressure injury are provided in Table IV. Based on this information, it is expected that the addition of the pressure-mitigation apparatus to the patient's treatment regime reduced overall healing time and patient comfort in comparison to the conventional techniques previously employed.

TABLE IV

Healing trajectory of a stage 4 pressure injury.

|  | Length (cm) | Width (cm) | Depth (cm) | Volume (cm$^3$) | Percentage Healed from Previous Month | Percentage Healed from Initiation of Pressure-Mitigation Apparatus |
|---|---|---|---|---|---|---|
| January | 2.0 | 1.3 | 0.6 | 1.6 | 39% | N/A |
| February | 2.2 | 1.2 | 0.5 | 1.3 | 19% | 19% |
| March | 1.5 | 1.0 | 0.2 | 0.5 | 62% | 69% |
| April | 0.3 | 0.1 | 0.2 | 0.006 | 99% | 99% |
| May | 0.0 | 0.0 | 0.0 | 0.0 | 100% | 100% |

Another study was performed to assess pressure injury prevention suing pressure-mitigation systems as disclosed herein. More specifically, the study compared the hospital-acquired pressure injury incidence in a group of patients utilizing the pressure-mitigation systems disclosed herein in conjunction with the standard of care to a control group receiving only the standard of care prevention measures (i.e., intermittent turning of the patient). (Jitendra B. Bharucha et al., *A Prospective Randomized Clinical Trial of a Novel, Noninvasive Perfusion Enhancement System for the Prevention of Hospital-Acquired Sacral Pressure Injuries*. J. Wound Ostomy Continence Nurs. 310-318 (2018).) The study enrolled 431 patients, and 399 patients completed the study. In the experimental group, the majority of the withdrawals were due to the noise from the pressure-mitigation apparatus or the sensation due to the continuous movement beneath the sacral region. Patients in the control group were treated in accordance with a methodology referred to as a "S.K.I.N." Bundle (S—surface selection, K—keep turning, I—incontinence management, N—nutrition), promulgated by the Ascension Health System. Patients in the experimental group were given the pressure-mitigation apparatuses described herein. Both groups otherwise received an identical standard of care, and all care measures were documented in an electronic health record (EHR) system.

As shown in Table V, the characteristics of the control and experimental groups were statistically similar with respect to age, Braden Scale score, and body mass index (BMI). Patients in the study ranged in age from 24 to 100 years.

TABLE V

Characteristics of trial participants.

|  | Control Group | Experimental Group |
| --- | --- | --- |
| Total Number of Patients Finished Trial | 213 | 186 |
| Hospital-Acquired Pressure Injury Incidence | 11 | 2 |
| Age Range | 35-98 | 24-100 |
| Mean Age | 74.38 | 74.69 |
| Mean Braden Scale Score | 14.5 | 14.2 |
| Male Patients | 79 (37.1%) | 94 (50.6%) |
| Mean BMI | 27.9 | 28.3 |
| Mean Length of Stay | 9.328 | 8.667 |

There were a wide range of discharge diagnoses (i.e., reasons why the individuals initially received the pressure injuries) for the trial participants, although there was no statistical difference between discharge diagnoses in the control and experimental groups. The top primary diagnoses at discharge were sepsis (n=71; 17.8% of all subjects in the trial), respiratory failure (n=36; 9%), septic shock (n=32; 8%), stroke (n=31; 7%), and acute kidney injury (n=18; 4.5%). Upon competition of the study, it was evident that the patients in the experimental group received clinically significant benefits in comparison to the patients in the control group. For example, eleven patients (5.16%) in the control group versus two patients (1.07%) in the experimental group developed hospital-acquired, sacral-region pressure injuries beyond what these patients already had. The difference between pressure injury incidence rates of the control and experimental groups was statistically significant (P=0.024). The mean length-of-stay (LOS) for all patients in the control group was 9.328 days, while the mean LOS for all patients in the experimental group was 8.667 days. Thus, the average LOS of the experimental group was roughly 0.66 days (7.1%) less than the control group, which not a statistically significant difference (P=0.46). However, when the mean LOS was examined by discharge diagnosis, it was discovered that the majority of the reduction in mean LOS seen in the experimental group was concentrated amongst those patients with one of two discharge diagnoses: stroke (n=31; 7.8%) and acute kidney injury (n=18; 4.5%). For these patients, the mean LOS in the experimental group was 5.865 days, and the mean LOS in the control group was 13.747 days. This difference was statistically significant (P=0.045). Accordingly, in this large-scale study, the pressure-mitigation systems have been shown to reduce the likelihood of hospital-acquired, sacral-region pressure injuries, as well as reduce the mean LOS for stroke and acute kidney injury.

Processing System

Figure 12:
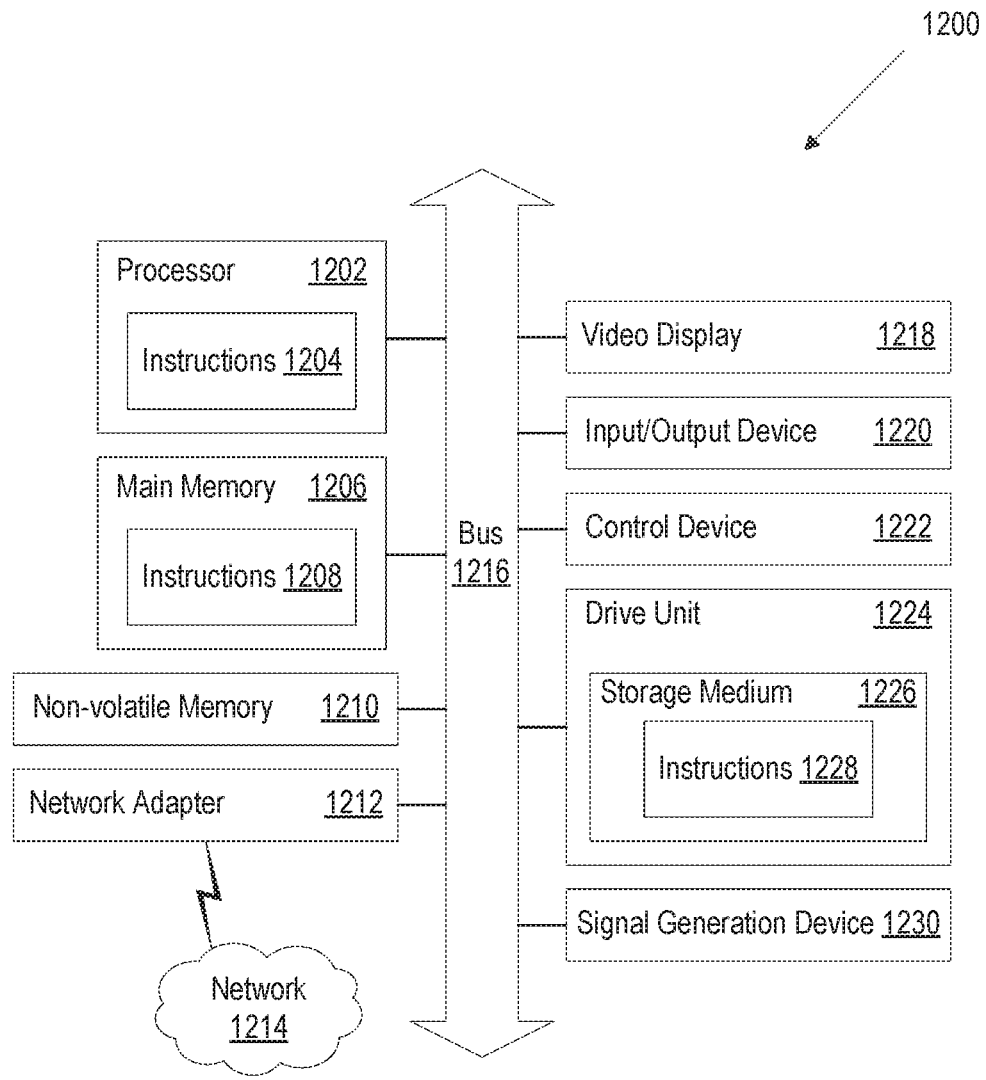
FIG. 12 is a block diagram illustrating an example of a processing system in which at least some operations described herein can be implemented.

FIG. 12 is a block diagram illustrating an example of a processing system 1200 in which at least some operations described herein can be implemented. For example, some components of the processing system 1200 may be hosted on a control system (e.g., control system 130 of FIG. 1) responsible for controlling a pressure mitigation support apparatus (e.g., pressure mitigation support apparatus 120 of FIG. 1).

The processing system 1200 may include one or more central processing units ("processors") 1202, main memory 1206, non-volatile memory 1210, network adapter 1212 (e.g., network interface), video display 1218, input/output devices 1220, control device 1222 (e.g., keyboard and pointing devices), drive unit 1224 including a storage medium 1226, and signal generation device 1230 that are communicatively connected to a bus 1216. The bus 1216 is illustrated as an abstraction that represents one or more physical buses and/or point-to-point connections that are connected by appropriate bridges, adapters, or controllers. The bus 1216, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1200 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 1200.

While the main memory 1206, non-volatile memory 1210, and storage medium 1226 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1228. The term "machine-readable medium" and "storage medium" shall also be taken to include any medium that is capable of storing, encoding, or carrying a set of instructions for execution by the processing system 1200.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1204, 1208, 1228) set at various times in various memory and storage devices in a computing device. When read and executed by the one or more processors 1202, the instruction(s) cause the processing system 1200 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1210, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1212 enables the processing system 1200 to mediate data in a network 1214 with an entity that is external to the processing system 1200 through any communication protocol supported by the processing system 1200 and the external entity. The network adapter 1212 can include a network adaptor card, a wireless network interface card, a router, an access point, a wireless router, a switch, a multilayer switch, a protocol converter, a gateway, a bridge, a bridge router, a hub, a digital media receiver, and/or a repeater.

The network adapter 1212 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Integrated Components

In one embodiment, in addition to the "user orienting" features of the side walls which acts to hold or secure the user over a pressure reduction surface (PRS) or perfusion enhancer surface such as, for example, the pressure mitigation support apparatus 120 of FIG. 1, in a specific orientation in order to maximize the pressure reduction and redistribution qualities of the surface, the elevated side walls can also act to hold or secure the user over the entirety of the air cells of the PRS such that no portion of the air cells of the PRS is uncovered. In other words, no portion of the air cells extend beyond the downward force of the user. If the air cells are allowed to extend beyond the downward force, and therefore not be completely covered by the user, then the air within the air cells could preferentially fill the portion of the air cell which remained uncovered by the user causing a "ballooning effect" of the uncovered portion of the air cell at the portion not covered by the user.

In one embodiment, the PRS is designed to fit to the size of the user (or fitted). The ballooning of the uncovered portion of the air cells can defeat the lifting effect produced by the air cells that occurs when the air cell is covered in its entirety by the user. Thus, as a result of the ballooning, increased air pressure within the air cells can be required to create the desired lifting of the user. Accordingly, in some instances, the lowest possible internal air pressure that could be used to lift the user may not be effective in this regard and additional, higher internal pressures could be necessary to perform the lifting. The increased pressures that would defeat the pressure reducing aim of the device. The side walls act to keep the user on top of the PRS as well as orient the user over that surface. If the side wall did not exist to frame the PRS, then the user would be free to move off the PRS allowing ballooning of the air cells on the opposite side and in addition the anatomy of the user's sacral region would not be in correct alignment with the geometry of the PRS. The side walls therefore function in this dual capacity.

In one embodiment, the inflatable portion of the device can have a specific orientation on top of the mattress or chair upon which it rests such that there is a side specific to the user contact and a side that is specific to the contact of the surface upon which it rests. In this example, the upward facing side of the PRS has a covering which is breathable and suited for direct skin contact while the down side of the PRS that is in contact with the mattress or chair is covered with a less non-porous material which has a reduced coefficient of friction that is less suitable for direct skin contact. The result of this construction can act to protect the user from the negative effects of shear strain on the skin as the device will preferentially slide over the underlying surface as the user stays in position with respect to the device. This construction can also act to prevent the user from moving from the proper orientation over the PRS of the inflatable portion of the device.

In one embodiment, the maximum pressure reduction and redistribution by the PRS is achieved when the user is oriented in a specific location over the pattern of the PRS. The side walls can control the users location over the surface in the x axis while the bed, when in a V-position with the legs elevated and the head elevated, acts to center the user over the PRS in the y axis.

In one embodiment, the apparatus consists consisting of an inflatable portion (pressure relieving surface), connector tubing and a computer controlled air pump can be incorporated into a support surface such as a mattress. In one embodiment, the additional components can be incorporated or integrated into support surface (e.g., reside within or under the support surface). Alternatively, the additional components can be attached to the outer surface of the support surface or mattress such the components become an integral part of the support surface without being inside the support surface. For example, the component can be attached to or attachable to the bed frame which supports the support surface or mattress. Alternatively or additionally, some or all of the components can also rest passively on the support surface without being physically attached to the support surface.

In one embodiment, the addition of the device (or apparatus) to the support surface enhances the functional pressure relief characteristics of the support surface to which it is added or attached or inserted into.

In one embodiment, the combination of the device and a support surface will not affect the ability of the device to perform its intended function as a pressure relief surface that is designed to orient the users anatomy with respect to the pattern of the pressure relief surface of the device through the use of elevated side walls intended to hold the users location in a specific manner. The location specific relationship will enhance the pressure relief capabilities of the device.

Computer-Controlled Pump

In one embodiment, a computer controlled pump that controls the inflatable portion of the device can be programmed with the specific weight of the user so as to deliver the correct user-specific pressures required for optimal pressure relief and redistribution for that particular user. The pump can continuously adjust the air pressures within the inflatable portion of the device so as to achieve predetermined preset internal air pressures within the air cells in order to achieve the optimal interface pressures between the user and the pressure relief surface of the device. This process is accomplished by continuously adding or removing air from the air cells to adjust to the varying load placed on the pressure relief surface by the user.

In one embodiment, the position of the user (e.g., supine, 30 degrees, 90 degrees) is entered into the pump along with the weight of the user so as to calculate the ideal internal air pressures of the air cell of the pressure relief surface to produce the ideal pressure relief characteristic for the device. That is the information is provided to a pump control device which generates a program that indicates appropriate pressures for each of the air cells over time. The pump control device then continuously controls the pump to provide the continuously changing pressures that are indicated by the program.

In one embodiment, the specific nature (e.g., of the stretcher pad—less than 3 inches, standard hospital mattress-non powered more than 3 inches, alternating pressure air mattress, etc.) of the support surface on which the inflatable overlay rests is entered into the computer controlled air pump in order to calculate the ideal internal pressure for the air cell of the pressure relief surface in order to produce the most effective pressure relief and redistribution.

In one embodiment, the pre-determined pressure time cycle programmed into the pump is used to coordinate the inflation and deflation of each air cell with respect to each other air cell of the inflatable portion of the device so as to produce an effective pressure relief and redistribution surface. The exact internal air pressures for a specific user can be calculated based the weight of that specific user, the surface the overlay is resting on, and the position of the bed (e.g., 0 degree, 30 degree, 90 degree) on which the overlay rests or is incorporated into. There is an algorithm programmed into the pump which calculates the exact pressures used for each user based on these variable that are entered for each user.

In one embodiment, the pump can acquire the programmable data regarding utilization, and this data can be sent via direct download or wirelessly to the computer controlled pump from a central database.

In one embodiment, the pump can utilize a silent valve system so as not to disturb the user.

In one embodiment, the air circulation portion of the inflatable overlay is comprised of a perforated sheet that covers the pressure relief surface and is supplied by a separate low pressure high flow pump to produce air circulating between the surface of the overlay and the user at the interface of the two. In this example, the chamber supplied with high flow low pressure air has no pressure relief capabilities and does not represent low air loss from the pressure relief air cells that are responsible for support of the weight of the user as in a low air loss configuration where the air in circulation between the user and the support surface is leaked directly from the pressure relieving air cells of the support surface.

In one embodiment, there is a pop off valve in the inflated side wall air cell which contains in a specific location the user over the pressure relief surface of the overlay such that if there is excess pressure placed on the side air wall the internal air is vented from the side air wall so as to prevent a blow out of the side air cell.

In one embodiment, the device can be used solely for the purpose of comfort of the user. For example, the device can be used during travel to prevent soreness and/or fatigue associated with long trips such as on airplane or bus or car.

In one embodiment, the pump and/or controller can be powered by ac or dc current.

In one embodiment, the device system with one or more of the pump, tubing, and inflatable portion (as described in the original non provisional) can be powered by one or more batteries.

In one embodiment, the device can be attached to any support surface, i.e., a chair or a bed. Alternatively or additionally, the device can be incorporated into any support surface, i.e., a bed or a chair. Alternatively or additionally, or the device can placed on top of any support surface i.e., a bed or a chair.

In one embodiment, the side walls act to hold the user over the PRS such that the entire surface area of the air cells that comprise the PRS is covered by the downward force of the user in order to prevent the ballooning of the air cells in areas not covered by the user by leaving no portion of the air cells uncovered at any location in order to increase the ability to reduce and redistribute interface pressure at the lowest internal air cell pressures possible.

In one embodiment, the side of the inflatable portion of the device that is in contact with the user's skin is breathable and the portion that is in contact with the surface upon which it rests is non-porous and has a low coefficient of friction so as to reduce the shear at the interface between the user and the device while this enables the user to remain in the proper orientation over the PRS of the device.

In one embodiment, a contact pressure mitigation support apparatus includes a pressure-mitigating contact portion and a plurality of elevated side support portions. The pressure-mitigating contact portion is interconnected on a base material and includes a plurality of independently pressurized chambers configured in a specific geometric pattern that is designed to mitigate contact pressure between a support surface (e.g., bed or chair) and a specific anatomic region of a patient's body when the specific anatomic region of the patient's body is oriented over an epicenter of the geometric pattern. The plurality of elevated side support portions is also interconnected on the base material and configured to actively orient the specific anatomic region of the patient's body over the epicenter of the geometric pattern.

In an embodiment, the contact pressure between the support surface and the specific anatomic region of the patient's body is mitigated by alternating the pressure in one or more of the plurality of independently pressurized relief chambers.

In an embodiment, the elevated side support portions are configured to actively orient the specific anatomic region of the patient's body over the epicenter of the geometric pattern when pressurized.

In an embodiment, the contact pressure mitigation support apparatus further includes one or more straps interconnected on the base material, wherein the one or more straps are configured to secure the pressure mitigation support apparatus to the support surface.

In an embodiment, the contact pressure mitigation support apparatus further includes a position sensor interconnected on the base material. The position sensor is configured to confirm that the specific anatomic region of the patient's body is oriented over the epicenter of the geometric pattern.

In an embodiment, the contact pressure mitigation support apparatus further includes a radio frequency (RF) transceiver interconnected on the base material and configured to wirelessly transmit the confirmation that the specific anatomic region of the patient's body is over the epicenter of the geometric pattern and/or receive instructions for individual chamber pressurization, etc.

In an embodiment, the pressure-mitigating contact portion is contoured to fit the patient's surface topography in the sacral region.

In an embodiment, to fit the patient's surface topography, the plurality of independently pressurized relief chambers are shorter in height in the center of the pressure-mitigating contact portion and taller in height on the edges of the pressure-mitigating contact portion.

In an embodiment, a surface area of the pressure-mitigating contact portion is designed to match the size of contact with the specific anatomic region of the patient's body.

In an embodiment, a surface area of the pressure-mitigating contact portion is designed to be less than the size of contact with the specific anatomic region of the patient's body.

In an embodiment, the length and the width of the pressure-mitigating contact portion are between fifteen and thirty inches.

In an embodiment, the plurality of elevated side support portions are elevated two or more inches in vertical height above the average surface height of the pressure-mitigating contact portion.

In an embodiment, the plurality of elevated side support portions are elevated in vertical height above the average surface height of the pressure-mitigating contact portion so as to create a barrier to lateral movement.

In an embodiment, the side support portions comprise independently pressurized chambers.

In an embodiment, the side support portions include a recess to support the patient's elbow.

In an embodiment, the independently pressurized relief chambers are configured to be independently pressurized with a gas.

In an embodiment, the independently pressurized chambers are configured to be independently pressurized with a liquid.

In an embodiment, the support surface comprises a mattress.

In an embodiment, the specific anatomic region of the patient's body comprises the sacral region.

In an embodiment, to actively orient the specific anatomic region of the patient's body over the epicenter of the geometric pattern, the plurality of side support portions are configured to confine lateral movement of the patient.

In an embodiment, to actively orient the specific anatomic region of the patient's body over the epicenter of the geometric pattern, the epicenter of the geometric pattern is overlaid on a V-shape in the support surface such that the epicenter of the apparatus resides over the low point of the support surface that is conformed into the V-shape upon which the apparatus rests.

In an embodiment, the anatomic region of the patient's body is segmented into various sub-regions and the geometric pattern is configured such that each of the independently pressurized chambers correspond to one of the various sub-regions.

In an embodiment, the independently pressurized chambers fit to the corresponding sub-region.

In an embodiment, the geometric pattern is symmetric and non-repeating in nature.

In an embodiment, the contact pressure mitigation support apparatus includes one or more channel tubes interconnected on the base material, the channel tubes configured to deliver pressure to the independently pressurized relief chambers.

In an embodiment, the contact pressure mitigation support apparatus includes one or more channel tubes interconnected on the base material, the channel tubes can be configured to deliver a gas (i.e., air or oxygen.) from one or more openings in the channel tubes. In this case, the channel tubes are not part of the pressure relieving surface (i.e., low air loss surface) and the gas delivered from the channel tubes is from a source independent from the pressure controlled supply of gas to the pressurized relief surfaces. That is, the gas delivered by the channel tubes is high volume and under volume control regulation.

In an embodiment, the one or more channel tubes follow seams between the independently pressurized relief chambers.

In an embodiment, the seams are recessed between the independently pressurized relief chambers when one or more of the independently pressurized relief chambers is pressurized.

In one embodiment, a partial body alternating contact pressure mattress overlay device is disclosed. The partial body alternating contact pressure mattress overlay device includes a plurality of independently pressurized chambers, a plurality of elevated side supports, and one or more straps. The plurality of independently pressurized chambers are configured in a geometric pattern that mitigates contact pressure between a support surface and a specific anatomic region of a patient's body when the specific anatomic region is oriented over an epicenter of the geometric pattern. The plurality of elevated side support portions are configured to actively orient the specific anatomic region over the epicenter of the geometric pattern. The one or more straps are configured to secure the pressure mitigation support device to the support surface.

In an embodiment, the partial body alternating contact pressure mattress overlay device further includes a radio frequency identification (RFID) detector configured to configured to detect whether the specific anatomic region of the patient's body is over the epicenter of the geometric pattern.

In an embodiment, the partial body alternating contact pressure mattress overlay device further includes one or more pressure sensors configured to detect the real-time pressure of each of the independently pressurized chambers.

In one embodiment, an alternating contact pressure mattress includes a mattress, a pressure-mitigating contact portion and a plurality of elevated side support portions. The pressure-mitigating contact portion includes a plurality of independently pressurized relief chambers interconnected on the mattress, wherein the independently pressurized relief chambers are configured in a geometric pattern that mitigates contact pressure between a support surface and a specific anatomic region of a patient's body when the specific anatomic region of the patient's body is oriented over an epicenter of the geometric pattern. The plurality of elevated side support portions are interconnected on the mattress and configured to actively orient the specific anatomic region of the patient's body over the epicenter of the geometric pattern.

In one embodiment, a contact pressure mitigation system is disclosed. The contact pressure mitigation system includes a pressure-mitigating support apparatus and a controller. The pressure-mitigating support apparatus includes a base material, a pressure-mitigating contact portion including a plurality of independently pressurized relief chambers interconnected on the base material, wherein the independently pressurized relief chambers are configured in a geometric pattern that mitigates contact pressure between a support surface and a specific anatomic region of a patient's body when the specific anatomic region of the patient's body is oriented over an epicenter of the geometric pattern, and a plurality of elevated side support portions interconnected on the base material, wherein the elevated side support portions are configured to actively orient the specific anatomic region of the patient's body over the epicenter of the geometric pattern. The controller is configured to regulate the pressure of each of the independently pressurized relief chambers.

In one embodiment, a contact pressure-mitigation support apparatus includes a base material, a pressure-mitigating contact portion, and a biocompatible adhesive portion. The pressure-mitigating contact portion can include a plurality of independently pressurized relief chambers interconnected on the base material. The independently pressurized relief chambers can be configured in a geometric pattern that mitigates contact pressure between a support surface and a specific anatomic region of a patient's body when pressure in the independently pressurized relief chambers is alternated and the specific anatomic region of the patient's body is oriented over an epicenter of the geometric pattern. The biocompatible adhesive portion interconnected on the base material is configured to actively orient the specific anatomic region of the patient's body over the epicenter of the geometric pattern.

In an embodiment, the biocompatible adhesive portion extends along at least a section of the perimeter of the contact pressure-mitigation support apparatus. The adhesive may be in direct contact with the skin of the user.

In an embodiment, the biocompatible adhesive portion extends along at least a section of one or more of the plurality of the independently pressurized relief chambers.

EXAMPLES

Several aspects of the present technology are set forth in the following examples.

1. A system comprising:
   a pressure-mitigation apparatus that includes a geometric arrangement of inflatable chambers formed by interconnections between a top layer and a bottom layer, wherein the inflatable chambers are configured to mitigate contact pressure applied to a human body by a support surface when pressure in the plurality of inflatable chambers is varied;
   a pump fluidly coupled to the chambers and configured to shift a main point of the contact pressure along a surface of the human body by sequentially varying the pressure in different subsets of the inflatable chambers; and
   a controller operably coupled to the pump and configured to regulate air flow provided by the pump.

2. The system of example 1 wherein the top layer is comprised of a first material configured for direct contact with the human body, and wherein the bottom layer is comprised of a second material configured for direct contact with the support surface.

3. The system of example 1 wherein the controller is configured to regulate the air flow provided by the pump based on a weight of the human body.

4. The system of example 3 wherein the weight of the human body is programmable by an individual via an interface generated by the controller.

5. The system of example 1 wherein, upon deployment of the pressure-mitigation apparatus, the inflatable chambers are naturally in an inflated state.

6. The system of example 5 wherein the inflatable chambers are configured to mitigate the contact pressure on an anatomical region of the human body over time in accordance with a programmable cycle associated with the anatomical region, and wherein the programmable cycle causes contact pressure on the anatomical region to be lessened by controllably deflating at least one inflatable chamber positioned beneath the anatomical region.

7. The system of example 1 wherein, upon deployment of the pressure-mitigation apparatus, the inflatable chambers are naturally in a deflated state.

8. The system of example 7 wherein the inflatable chambers are configured to mitigate the contact pressure on an anatomical region of the human body over time in accordance with a programmable cycle associated with the anatomical region, and wherein the programmable cycle causes contact pressure on the anatomical region to be lessened by controllably inflating at least one inflatable chamber positioned adjacent the anatomical region.

9. The system of example 1, further comprising:
   a wedge configured to actively orient an anatomical region of the human body lengthwise over an epicenter of the geometric arrangement.

10. The system of example 1, further comprising:
   an elevated side support configured to actively orient an anatomical region of the human body widthwise over the epicenter of the geometric pattern.

11. The system of example 10, further comprising:
   a pop-off valve interconnected on the elevated side support,
      wherein the pop-off valve is configured to release air from the elevated side support in response to excess pressure on the elevated side support.

12. The system of example 10, wherein the elevated side support extends longitudinally along at least one side of the pressure-mitigation apparatus.

13. An apparatus for mitigating a contact pressure applied by a support surface to a specific anatomic region of a human body supported by the support surface, the apparatus comprising:
   a first portion designed to face the support surface;
   a second portion designed to face the human body supported by the support surface; and
   a geometric arrangement of inflatable chambers formed via interconnections between the first and second portions,
      wherein each inflatable chamber can be independently pressurized via a discrete airflow, and
      wherein, upon deployment of the apparatus, a main point of contact pressure applied by the support surface to the human body is moved amongst a plurality of locations by sequentially varying the pressure in different predetermined subsets of the inflatable chambers.

14. The apparatus of example 13 wherein each predetermined subset includes at least one inflatable chamber.

15. The apparatus of example 13 wherein the main point of contact pressure is moved amongst the plurality of locations in accordance with a predetermined pattern.

16. The apparatus of example 13 wherein the main point of contact pressure is moved amongst the plurality of locations in accordance with a random pattern or a semi-random pattern.

17. The apparatus of example 13 wherein, upon deployment of the apparatus, the inflatable chambers are naturally in an inflated state, and wherein the main point of contact pressure is moved amongst the plurality of locations by varying a location of at least one deflated chamber.

18. The apparatus of example 13 wherein, upon deployment of the apparatus, the inflatable chambers are naturally in a deflated state, and wherein the main point of contact pressure is moved amongst the plurality of locations by varying a location of at least one inflated chamber.

19. A method for treating a human body, the method comprising:
    diagnosing a condition affecting the human body that causes the human body to be at least partially immobilized on a support surface,
        wherein the support surface applies a contact pressure to the human body;
    identifying an appropriate treatment regimen for the condition;
    disposing a pressure-mitigation apparatus of a pressure mitigation system between the human body and the support surface,
        wherein the pressure-mitigation apparatus includes a geometric arrangement of inflatable chambers, and
        wherein the pressure mitigation system comprises a pump fluidly coupled to the inflatable chambers to deliver a discrete airflow into each of the inflatable chambers; and
    shifting a main point of contact pressure applied by the support surface to the human body by sequentially varying the airflow delivered to different subsets of the inflatable chambers.

20. The method of example 19 wherein shifting the main point of contact pressure comprises shifting the main point of contact pressure periodically to promote increased blood flow throughout an anatomical region of the human body supported by the pressure-mitigation apparatus.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A system comprising:
    a pressure-mitigation apparatus that includes a geometric arrangement of inflatable chambers formed by interconnections between a top layer and a bottom layer,
        wherein the inflatable chambers are configured to mitigate contact pressure applied to a human body by a support surface when pressure in the plurality of inflatable chambers is varied;
    a pump fluidly coupled to the inflatable chambers and configured to shift a main point of the contact pressure along a surface of the human body by sequentially varying the pressure in different subsets of the inflatable chambers; and
    a controller operably coupled to the pump and configured to regulate air flow provided by the pump.

2. The system of claim 1 wherein the top layer is comprised of a first material configured for direct contact with the human body, and wherein the bottom layer is comprised of a second material configured for direct contact with the support surface.

3. The system of claim 1 wherein the controller is configured to regulate the air flow provided by the pump based on a weight of the human body.

4. The system of claim 3 wherein the weight of the human body is programmable by an individual via an interface generated by the controller.

5. The system of claim 1 wherein, upon deployment of the pressure-mitigation apparatus, the inflatable chambers are naturally in an inflated state.

6. The system of claim 5 wherein the inflatable chambers are configured to mitigate the contact pressure on an anatomical region of the human body over time in accordance with a programmable cycle associated with the anatomical region, and wherein the programmable cycle causes contact pressure on the anatomical region to be lessened by controllably deflating at least one inflatable chamber positioned beneath the anatomical region.

7. The system of claim 1 wherein, upon deployment of the pressure-mitigation apparatus, the inflatable chambers are naturally in a deflated state.

8. The system of claim 7 wherein the inflatable chambers are configured to mitigate the contact pressure on an anatomical region of the human body over time in accordance with a programmable cycle associated with the anatomical region, and wherein the programmable cycle causes contact pressure on the anatomical region to be lessened by controllably inflating at least one inflatable chamber positioned adjacent the anatomical region.

9. The system of claim 1, further comprising:
a wedge configured to actively orient an anatomical region of the human body lengthwise over an epicenter of the geometric arrangement.

10. The system of claim 1, further comprising:
an elevated side support configured to actively orient an anatomical region of the human body widthwise over an epicenter of the geometric pattern.

11. The system of claim 10, further comprising:
a pop-off valve interconnected on the elevated side support,
wherein the pop-off valve is configured to release air from the elevated side support in response to excess pressure on the elevated side support.

12. The system of claim 10, wherein the elevated side support extends longitudinally along at least one side of the pressure-mitigation apparatus.

13. An apparatus for mitigating a contact pressure applied by a support surface to a specific anatomic region of a human body supported by the support surface, the apparatus comprising:
a first portion designed to face the support surface;
a second portion designed to face the human body supported by the support surface; and
a geometric arrangement of inflatable chambers formed via interconnections between the first and second portions,
wherein each inflatable chamber can be independently pressurized via a discrete airflow, and
wherein, upon deployment of the apparatus, a main point of contact pressure applied by the support surface to the human body is moved amongst a plurality of locations by sequentially varying the pressure in different predetermined subsets of the inflatable chambers.

14. The apparatus of claim 13 wherein each predetermined subset includes at least one inflatable chamber.

15. The apparatus of claim 13 wherein the main point of contact pressure is moved amongst the plurality of locations in accordance with a predetermined pattern.

16. The apparatus of claim 13 wherein the main point of contact pressure is moved amongst the plurality of locations in accordance with a random pattern or a semi-random pattern.

17. The apparatus of claim 13 wherein, upon deployment of the apparatus, the inflatable chambers are naturally in an inflated state, and wherein the main point of contact pressure is moved amongst the plurality of locations by varying a location of at least one deflated chamber.

18. The apparatus of claim 13 wherein, upon deployment of the apparatus, the inflatable chambers are naturally in a deflated state, and wherein the main point of contact pressure is moved amongst the plurality of locations by varying a location of at least one inflated chamber.

19. A method for treating a human body, the method comprising:
diagnosing a condition affecting the human body that causes the human body to be at least partially immobilized on a support surface,
wherein the support surface applies a contact pressure to the human body;
identifying an appropriate treatment regimen for the condition;
disposing a pressure-mitigation apparatus of a pressure mitigation system between the human body and the support surface,
wherein the pressure-mitigation apparatus includes a geometric arrangement of inflatable chambers, and
wherein the pressure mitigation system comprises a pump fluidly coupled to the inflatable chambers to deliver a discrete airflow into each of the inflatable chambers; and
shifting a main point of contact pressure applied by the support surface to the human body by sequentially varying the airflow delivered to different subsets of the inflatable chambers.

20. The method of claim 19 wherein shifting the main point of contact pressure comprises shifting the main point of contact pressure periodically to promote increased blood flow throughout an anatomical region of the human body supported by the pressure-mitigation apparatus.

* * * * *